US008492361B2

(12) United States Patent
Nguyen et al.

(10) Patent No.: US 8,492,361 B2
(45) Date of Patent: Jul. 23, 2013

(54) METHODS FOR TREATING NON-SMALL CELL LUNG CANCER USING 5-AZACYTIDINE

(75) Inventors: Aaron N. Nguyen, San Jose, CA (US); Kyle J. MacBeth, San Francisco, CA (US)

(73) Assignee: Celgene Corporation, Summit, NJ (US)

( * ) Notice: Subject to any disclaimer, the term of this patent is extended or adjusted under 35 U.S.C. 154(b) by 21 days.

(21) Appl. No.: 13/148,636

(22) PCT Filed: Feb. 9, 2010

(86) PCT No.: PCT/US2010/000361
§ 371 (c)(1),
(2), (4) Date: Sep. 13, 2011

(87) PCT Pub. No.: WO2010/093435
PCT Pub. Date: Aug. 19, 2010

(65) Prior Publication Data
US 2011/0319355 A1 Dec. 29, 2011

Related U.S. Application Data

(60) Provisional application No. 61/151,479, filed on Feb. 10, 2009.

(51) Int. Cl.
*A01N 43/04* (2006.01)
*A61K 31/70* (2006.01)
(52) U.S. Cl.
USPC .............................................. 514/49; 514/43
(58) Field of Classification Search
None
See application file for complete search history.

(56) References Cited

U.S. PATENT DOCUMENTS

| 2009/0286752 A1 | 11/2009 | Etter et al. |
| 2010/0311683 A1 | 12/2010 | Beach et al. |

FOREIGN PATENT DOCUMENTS

| WO | WO 2006/034154 | 3/2006 |
| WO | WO 2009/139888 | 11/2009 |
| WO | WO 2013/022872 A1 | 2/2013 |

OTHER PUBLICATIONS

Kamisskas et al. Clinical Cancer Research (2005), vol. 11, pp. 3604-3608.*
Glaser, 2007, "HDAC Inhibitors: Clinical Update and Mechanism-Based Potential," *Biochem. Pharm.*, 74, 659-71.
Juergens et al., 2009, "Interim Analysis of a Phase II Trial of 5-Azacytidine (5AC) and Entinostat (SNDX-275) in Relapsed Advanced Lung Cancer (NSCLC)," *Journal of Clinical Oncology*, 27, 15S, 8055.
Momparler, 2005, "Epigenetic Therapy of Cancer with 5-Aza-2'-Deoxycytidine (Decitabine)," *Seminars in Oncology*, 32(5), 443-451.
Quagliana et al., 1977, "Phase II Study of 5-Azacytidine in Solid Tumors," *Cancer Treatment Reports*, 61(1), 51-54.
Velez-Garcia et al., 1977, "Twice Weekly 5-Azacytidine Infusion in Disseminated Metastatic Cancer: A Phase II Study," *Cancer Treatment Reports*, 61(9), 1675-1677.
International Search Report dated May 12, 2010 in PCT/US2010/000361.
Aparicio et al., "Review of the Clinical Experience with 5-Azacytidine and 5-Aza-2'-Deoxycytidine in Solid Tumors," *Current Opinion in Investigational Drugs*, 2002, 3(4), 627-33.
Bellet et al., "Clinical Trial with Subcutaneously Administered 5-Azacytidine (NSC-102816)," *Cancer Chemotherapy Reports*, Part I, 1974, 58(2), 217-22.
Bellet et al., "Phase II Study of Subcutaneously Administered 5-Azacytidine (NSC-102816) in Patients with Metastatic Malignant Melanoma," *Medical and Pediatric Oncology*, 1978, 4, 11-15.
Bhuyan et al., "Cell Cycle Phase Specificity of Antitumor Agent," *Cancer Research*, 1972, 32, 398-407.
Bhuyan et al., "Cell-Kill Kinetics of Several S-Phase-Specific Drugs," *Cancer Research*, 1973, 33, 888-94.
Brock et al., "DNA Methylation Markers and Early Recurrence in Stage I Lung Cancer," *New England Journal of Medicine*, 2008, 358(11), 1118-28.
Christman et al., "5-Azacytidine and 5-Aza-2'-Deoxycytidine as Inhibitors of DNA Methylation: Mechanistic Studies and Their Implications for Cancer Therapy," *Oncogene*, 2002, 21, 5483-95.
Cowan et al., "Will DNA Methylation Inhibitors Work in Solid Tumors? A Review of the Clinical Experience with Azacitidine and Decitabine in Solid Tumors," *Epigenomics*, 2010, 2(1), 71-86.
Cunningham et al., "Comparison of 5-Azacytidine (NSC-102816) with CCNU (NSC-79037) in the Treatment of Patients with Breast Cancer and Evaluation of the Subsequent Use of Cyclophosphamide (NSC-26271)," *Cancer Chemotherapy Reports*, Part I, 1974, 58(5), 677-81.
Curt et al., "A Phase I and Pharmacokinetic Study of Dihydro-5-Azacytidine (NSC 264880)," *Cancer Research*, 1985, 45, 3359-63.
Das et al., "Methylation Mediated Silencing of TMS1/ASC Gene in Prostate Cancer," *Molecular Cancer*, 2006, 5(28), doi: 10.1186/1476-4598-5-28, available at http://www.molecular-cancer.com/content/5/1/28.
Dover et al., "5-Azacytidine Increases HbF Production and Reduces Anemia in Sickle Cell Disease: Dose-Response Analysis of Subcutaneous and Oral Dosage Regimens," *Blood*, 1985, 66(3), 527-32.
Fenaux et al., "Efficacy of Azacitidine Compared with that of Conventional Care Regimens in the treatment of Higher-Risk Myelodysplastic Syndromes: A Randomised, Open-Label, Phase III Study," *The Lancet Oncology*, 2009, 10(3), 223-32.
Garcia-Manero, "Demethylating Agents in Myeloid Malignancies," *Current Opinion in Oncology*, 2008, 20, 705-10.
Garcia-Manero et al., "A Pilot Pharmacokinetic Study of Oral Azacitidine," *Leukemia*, 22: 1680-84 (2008).
Garcia-Manero et al., "Phase I Study of Oral Azacitidine in Myelodysplastic Syndromes, Chronic Myelomonocytic Leukemia, and Acute Myeloid Leukemia," *Journal of Clinical Oncology*, 29(18): 2521-27 (2011).

(Continued)

*Primary Examiner* — Patrick Lewis
(74) *Attorney, Agent, or Firm* — Jones Day

(57) ABSTRACT

The present disclosure provides methods for treating subjects having non-small cell lung cancer, wherein the methods comprise administering to the subject a cytidine analog, such as 5-azacytidine. Also provided are methods relating to identification and treatment of particular non-small cell lung cancer types sensitive to particular cytidine analogs.

32 Claims, 18 Drawing Sheets

OTHER PUBLICATIONS

Gifford et al., "The Acquisition of hMLH1 Methylation in Plasma DNA After Chemotherapy Predicts Poor Survival for Ovarian Cancer Patients," *Clinical Cancer Research*, 2004, 10, 4420-26.

Howell et al., "Demethylating Agents in the Treatment of Cancer," *Pharmaceuticals*, 2010, 3(7), 2022-2044.

Israili et al., "The Disposition and Pharmacokinetics in Humans of 5-Azacytidine Administered Intravenously as a Bolus or by Continuous Infusion," *Cancer Research*, 1976, 36, 1453-61.

Jubb, et al., "Methylation and Colorectal Cancer," *Journal of Pathology*, 2001, 195, 111-34.

Kornblith et al., "Impact of Azacytidine on the Quality of Life of Patients with Myelodysplastic Syndrome Treated in a Randomized Phase III Trial: A Cancer and Leukemia Group B Study," *Journal of Clinical Oncology*, 2002, 20(10), 2441-52.

Kritz et al., "Pilot Study of 5-Azacytidine (5-AZA) and Carboplatin (CBDCA) in Patients with Relapsed/Refractory Leukemia," *American Journal of Hematology*, 51(2): 117-21 (1996).

Li et al., "Phase Specificity of 5-Azacytidine Against Mammalian Cells in Tissue Culture," *Cancer Research*, 1970, 30, 2770-75.

Lomen et al., "Phase I Study of 5-Azacytidine (NSC-102816) Using 24-Hour Continuous Infusion for 5 Days," *Cancer Chemotherapy Reports*, Part I, 1975, 59(6), 1123-26.

Moertel et al., "Phase II Study of 5-Azacytidine (NSC-102816) in the Treatment of Advanced Gastrointestinal Cancer," *Cancer Chemotherapy Reports*, Part I, 1972, 56(5), 649-52.

Neil et al., "Enhancement by Tetrahydrouridine (NSC-112907) of the Oral Activity of 5-Azacytidine (NSC-102816) in L1210 Leukemic Mice," *Cancer Chemotherapy Reports*, Part I, 1975, 59(3), 459-65.

Quagliana et al., "Phase II Study of 5-Azacytidine in Solid Tumor," *Cancer Treatment Reports*, 1977, 61(1), 51-54.

Shnider et al., "A Phase I Study of 5-Azacytidine (NSC-102816)," *Journal of Clinical Pharmacology*, 1976, 205-12.

Silverman et al., "Randomized Controlled Trials of Azacitidine in Patients with the Myelodysplastic Syndrome: A Study of the Cancer and Leukemia Group B," *Journal of Clinical Oncology*, 2002, 20(10), 2429-2440.

Silverman et al., "Further Analysis of Trials with Azacitidine in Patients with Myelodysplastic Syndrome: Studies 8421, 8921, and 9221 by the Cancer and Leukemia Group B," *Journal of Clinical Oncology*, 2006, 24(24), 3895-3903.

Skikne et al., "A Phase I, Open-Label, Dose-Escalation Study to Evaluate the Safety, Pharmacokinetics, and Pharmacodynamics of Oral Azacitidine in Subjects with Myelodysplastic Syndromes (MDS) or Acute Myelogenous Leukemia (AML)," *Journal of Clinical Oncology* (May 20, 2008 Supplement), 2008 ASCO Annual Meeting Proceedings (Meeting Date: May 30-Jun. 3, 2008), Part I, 2008, 26(15S), poster # 7091.

Srinivasan et al., "Phase II Study of 5-Azacytidine in Sarcomas of Bone," *American Journal of Clinical Oncology*, 1982, 5, 411-15.

Stoltz et al., "Development of an Oral Dosage Form of Azacitidine: Overcoming Challenges in Chemistry, Formulation, and Bioavailability," *Blood*, 48th ASH Annual Meeting (Meeting Date: Dec. 9-12, 2006), 108, poster # 4850.

Tan et al., "Clinical Trial of 5-Azacytidine (5-azaCR)," *American Association for Cancer Research*, 64th Annual Meeting, Abstract # 385, Apr. 11-13, 1973.

Troetel, et al., "Absorption, Distribution, and Excretion of 5-Azacytidine (NSC-102816) in Man," *Cancer Chemotherapy Reports*, Part I, 1972, 56(3), 405-11.

Velez-Garcia et al., "Twice Weekly 5-Azacytidine Infusion in Disseminated Metastatic Cancer: A Phase II Study," *Cancer Treatment Reports*, 1977, 61(9), 1675-77.

Vogler et al., "5-Azacytidine (NSC 102816): A New Drug for the Treatment of Myeloblastic Leukemia," *Blood*, 48(3): 331-37 (1976).

Ward et al., "An Oral Dosage Formulation of Azacitidine: A Pilot Pharmacokinetic Study," *Journal of Clinical Oncology* (Jun. 20, 2007 Supplement), 2007 ASCO Annual Meeting Proceedings (Meeting Date: Jun. 1-5, 2007), Part I, 2007, 25(18S), poster # 7084.

Zaitseva et al., "Convergent Syntheses and Cytostatic Properties of 2-Chloro-2'-Deoxy-2'-Fluoroadenosine and its $N^7$-Isomer," *Bioorg. & Med. Chem. Lett.*, 5(24): 2999-3002 (1995).

Ziemba et al., "Development of Oral Demethylating Agents for the Treatment of Myelodysplastic Syndromes," *American Association of Cancer Research*, 100th Annual Meeting, Apr. 18-22, Abstract #3369 (2009).

\* cited by examiner

METHODS FOR TREATING NON-SMALL CELL LUNG CANCER USING 5-AZACYTIDINE

This application is a §371 national phase application of International Patent Application No. PCT/US2010/000361, filed Feb. 9, 2010, which claims priority to U.S. Provisional Application No. 61/151,479, filed Feb. 10, 2009.

I. FIELD

Provided herein are methods for treating non-small cell lung cancer using a cytidine analog or a salt, solvate, hydrate, precursor, and/or derivative thereof. Certain of the methods provided herein comprise treating non-small cell lung cancer using a combination of two or more active agents, including 5-azacytidine.

II. BACKGROUND

Cancer is a major worldwide public health problem; in the United States alone, approximately 560,000 people died of cancer in 2006. See, e.g., U.S. Mortality Data 2006, National Center for Health Statistics, Centers for Disease Control and Prevention (2009). Many types of cancer have been described in the medical literature. Examples include cancer of blood, bone, skin, lung, colon, breast, prostate, ovary, brain, kidney, bladder, pancreas, and liver, among others. The incidence of cancer continues to climb as the general population ages and as new forms of cancer develop. A continuing need exists for effective therapies to treat subjects with cancer.

Non-small cell lung cancer (NSCLC) is a heterogeneous aggregate of histologies, including, e.g., epidermoid or squamous carcinoma, adenocarcinoma, and large cell carcinoma. Patients with NSCLC may be divided into three groups that reflect both the extent of the disease and the treatment approach: (1) patients with tumors that are surgically resectable; (2) patients with either locally or regionally advanced lung cancer; and (3) patients with distant metastases at the time of diagnosis. Current treatments for NSCLC include surgery, chemotherapy, and/or radiation therapy. As indicated by the National Cancer Institute, however, current methods of treating NSCLC are often unsatisfactory, and a need exists for effective therapies to treat subjects with NSCLC. See, e.g., Non-Small Cell Lung Cancer Treatment (PDQ®), U.S. National Institutes of Health, National Cancer Institute, available at http://www.cancer.gov.

Nucleoside analogs have been tested clinically for the treatment of certain cancers. The nucleoside analogs 5-azacytidine (also known as 4-amino-1-β-D-ribofuranosyl-1,3,5-triazin-2(1H)-one; National Service Center designation NSC-102816; CAS Registry Number 320-67-2; azacitidine; Aza and AZA; and currently marketed as VIDAZA®) and 2'-deoxy-5-azacytidine (also known as 5-aza-2'-deoxycytidine, decitabine, Dac, and DAC, and currently marketed as DACOGEN®) are DNA methyltransferase (DNMT) inhibitors that have been approved by the U.S. Food and Drug Administration for the treatment of myelodysplastic syndromes (MDS). Azacitidine and decitabine are cytidine analogs; a structural difference between these cytidine analogs and their related natural nucleosides is the presence of a nitrogen at position 5 of the cytosine ring in place of a carbon. Azacitidine may be defined as having a molecular formula of $C_8H_{12}N_4O_5$, a molecular weight of 244.21 grams per mole, and a structure as shown below. Decitabine may be defined as having a molecular formula of $C_8H_{12}N_4O_4$, a molecular weight of 228.21 grams per mole, and a structure as shown below.

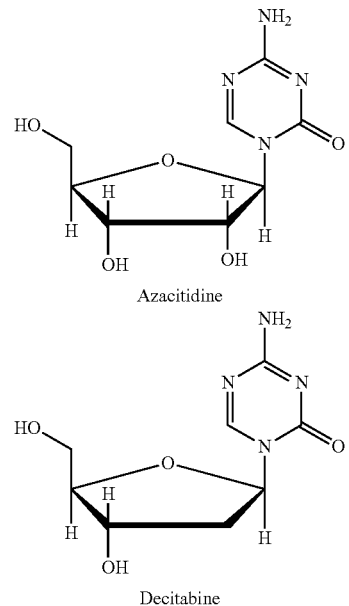

Azacitidine

Decitabine

Azacitidine and decitabine have been tested in clinical trials and showed significant anti-tumor activity, such as, for example, in the treatment of myelodysplastic syndromes (MDS), acute myelogenous leukemia (AML), chronic myelogenous leukemia (CML), acute lymphocytic leukemia (ALL), and non Hodgkin's lymphoma (NHL). See, e.g., Aparicio et al., Curr. Opin. Invest. Drugs 3(4): 627-33 (2002). Azacitidine has undergone NCI-sponsored trials for the treatment of MDS and has been approved for treating all FAB subtypes of MDS. See, e.g., Kornblith et al., J. Clin. Oncol. 20(10): 2441-52 (2002); Silverman et al., J. Clin. Oncol. 20(10): 2429-40 (2002). Azacitidine may alter the natural course of MDS by diminishing the transformation to AML through its cytotoxic activity and its inhibition of DNA methyltransferase. In a Phase III study, azacitidine significantly prolonged survival and time to AML transformation or death in elderly subjects. See, e.g., Silverman et al., Blood 106(11): Abstract 2526 (2005).

III. SUMMARY

Provided herein are methods for treating, preventing or managing NSCLC by administering one or more cytidine analogs to subjects having NSCLC. In certain embodiments, the methods comprise treating, preventing or managing certain types of NSCLC, including but not limited to, epidermoid or squamous cell carcinoma, large cell carcinoma, adenocarcinoma, adenosquamous carcinoma, carcinomas with pleomorphic, sarcomatoid or sarcomatous elements, carcinoid tumor, carcinomas of salivary-gland, and unclassified carcinoma. In certain embodiments, the methods comprise treating, preventing or managing certain stages of NSCLC, including but not limited to, occult carcinoma, Stage 0, Stage IA, Stage IB, Stage IIA, Stage IIB, Stage IIIA, Stage IIIB, and Stage IV, in a subject having NSCLC. In certain embodiments, the methods comprise treating or managing NSCLC in a subject having particular NSCLC cell types. In certain embodiments, the cytidine analog is 5-azacytidine (azacitidine). In certain embodiments, the cytidine analog is 5-aza-2'-deoxycytidine (decitabine). In certain embodiments, the methods comprise co-administering two or more active agents. In certain embodiments, the methods comprise treating, preventing or managing NSCLC using one or more of the methods provided herein, together with one or more of the treatments selected from surgery, chemotherapy, immunotherapy, targeted therapy, and radiation therapy.

Particular embodiments herein provide methods of treating certain NSCLC cell types, including but not limited to, A549, H1975, H23, H460, and/or H1299, in a subject having NSCLC. Particular methods comprise identifying the presence of at least one NSCLC cell type, including but not limited to, A549, H1975, H23, H460, and/or H1299, in a subject having NSCLC. Particular methods comprise administering one or more cytidine analogs to a subject having NSCLC to treat one or more NSCLC cell types, including but not limited to, A549, H1975, H23, H460, and/or H1299. Particular methods comprise administering 5-azacytidine to a subject having NSCLC to treat one or more NSCLC cell types, including but not limited to, A549, H1975, H23, H460, and/or H1299. Particular embodiments herein provide methods for treating a subject with NSCLC by administering 5-azacytidine to the subject, wherein the NSCLC includes a cell type selected from A549, H1975, H23, H460, and H1299.

Particular embodiments herein provide methods of treating, preventing or managing certain types of NSCLC, including but not limited to, (1) squamous cell carcinoma, including but not limited to, papillary, clear cell, small cell, and basaloid carcinoma; (2) adenocarcinoma, including but not limited to, acinar, papillary, bronchioloalveolar carcinoma (nonmucinous, mucinous, mixed mucinous and nonmucinous or indeterminate cell type), solid adenocarcinoma with mucin, adenocarcinoma with mixed subtypes, and other variants including well-differentiated fetal adenocarcinoma, mucinous (colloid) adenocarcinoma, mucinous cystadenocarcinoma, signet ring adenocarcinoma, and clear cell adenocarcinoma; (3) large cell carcinoma, including but not limited to, large cell neuroendocrine carcinoma, combined large cell neuroendocrine carcinoma, basaloid carcinoma, lymphoepithelioma-like carcinoma, clear cell carcinoma, and large cell carcinoma with rhabdoid phenotype; (4) adenosquamous carcinoma; (5) carcinomas with pleomorphic, sarcomatoid, or sarcomatous elements, including but not limited to, carcinomas with spindle and/or giant cells, spindle cell carcinoma, giant cell carcinoma, carcinosarcoma, and pulmonary blastoma; (6) carcinoid tumor, including but not limited to, typical carcinoid and atypical carcinoid; (7) carcinomas of salivary-gland, including but not limited to, mucoepidermoid carcinoma and adenoid cystic carcinoma; and (8) unclassified carcinoma. Particular embodiments herein provide methods of treating, preventing or managing NSCLC in the primary tumor, lymph nodes, and/or distant metastasis, in a subject having NSCLC. Particular embodiments herein provide methods of treating NSCLC in a subject having surgically resectable NSCLC, locally or regionally advanced NSCLC, and/or distant metastatic NSCLC.

Certain methods herein provide administration of the cytidine analog by, e.g., intravenous (IV), subcutaneous (SC) and/or oral routes of administration. Certain embodiments herein provide co-administration of a cytidine analog (e.g., 5-azacytidine) with one or more additional active agents to provide a synergistic therapeutic effect in subjects in need thereof. The co-administered agent(s) may be a cancer therapeutic agent, as described herein. In certain embodiments, the co-administered agent(s) may be dosed, e.g., orally or by injection.

IV. BRIEF DESCRIPTION OF THE DRAWINGS

V. DETAILED DESCRIPTION

Figure 1:
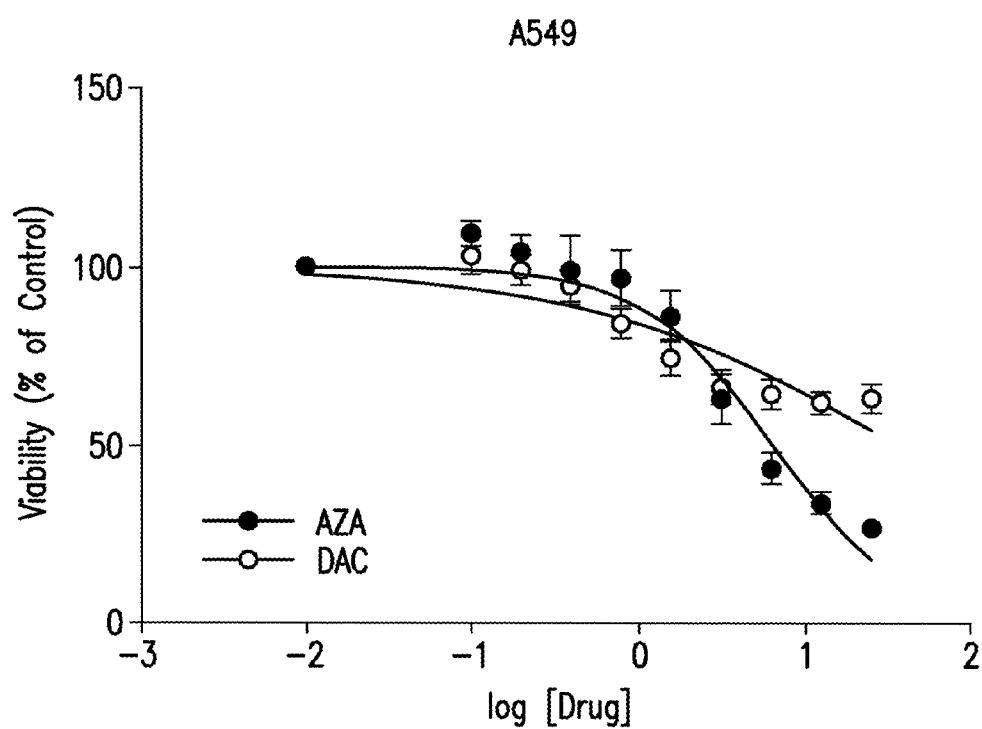
FIG. 1 represents effects of AZA and DAC on the viability of A549 cells.

Unless defined otherwise, all technical and scientific terms used herein have the same meaning as commonly understood by one of ordinary skill in the art. All publications and patents referred to herein are incorporated by reference herein in their entireties.

5.1 Definitions

As used in the specification and the accompanying claims, the indefinite articles "a" and "an" and the definite article "the" include plural as well as singular referents, unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the diagnosis or the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. In certain embodiments, subjects with familial history of a disease are potential candidates for preventive regimens. In certain embodiments, subjects who have a history of recurring symptoms are also potential candidates for prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, and unless otherwise specified, "amelioration" of the symptoms of a particular disorder by administration of a particular pharmaceutical composition refers to any lessening, whether permanent or temporary, lasting or transient, that can be attributed to or associated with the administration of the composition.

As used herein, and unless otherwise specified, the term "therapeutically effective amount" or "effective amount" of a compound means an amount sufficient to provide a therapeutic benefit in the treatment or management of a disease or disorder, or to delay or minimize one or more symptoms associated with the disease or disorder. A "therapeutically effective amount" or "effective amount" of a compound means an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces, delays, or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

As used herein, and unless otherwise specified, the term "subject" is defined herein to include animals such as mammals, including, but not limited to, primates (e.g., humans), cows, sheep, goats, horses, dogs, cats, rabbits, rats, mice, and the like. In specific embodiments, the subject is a human. The terms "subject" and "patient" are used interchangeably herein in reference, for example, to a mammalian subject, such as a human. In particular embodiments, a subject having NSCLC is a subject who has been previously diagnosed as having NSCLC.

As used herein, and unless otherwise specified, "tumor" refers to all neoplastic cell growth and proliferation, whether malignant or benign, and all pre-cancerous and cancerous cells and tissues. As used herein, and unless otherwise specified, "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the terms "cancer" and "cancerous" refer to or describe the physiological condition in mammals that is typically characterized by unregulated cell growth. Examples of cancer include, but are not limited to, lymphoma, leukemia, and solid tumors, such as, for example, lung cancer.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

As used herein, and unless otherwise specified, the term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

As used herein, and unless otherwise specified, the term "anticancer agent" or "cancer therapeutic agent" is meant to include anti-proliferative agents and chemotherapeutic agents, including, but not limited to, antimetabolites (e.g., 5-fluoro uracil, methotrexate, fludarabine, cytarabine (also known as cytosine arabinoside or Ara-C), and high dose cytarabine), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitabine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), and mitoxantrone), topoisomerase inhibitors (e.g., etoposide and camptothecins), purine antagonists or pyrimidine antagonists (e.g., 6-mercaptopurine, 5-fluorouracil, cytarabine, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone; methylprednisolone, tamoxifen, leuprolide, flutamide, and megestrol), monoclonal antibodies (e.g., gemtuzumab ozogamicin, alemtuzumab, rituximab, and yttrium-90-ibritumomab tiuxetan), immuno-modulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, and agents to attenuate any adverse effects (e.g., antiemetics).

As used herein, and unless otherwise specified, the terms "co-administration" and "in combination with" include the administration of two or more therapeutic agents simultaneously, concurrently or sequentially within no specific time limits unless otherwise indicated. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, and unless otherwise specified, the terms "composition," "formulation," and "dosage form" are intended to encompass products comprising the specified ingredient(s) (in the specified amounts, if indicated), as well as any product(s) which result, directly or indirectly, from combination of the specified ingredient(s) in the specified amount(s).

As used herein, and unless otherwise specified, the term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. In one embodiment, by "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. See, e.g., Remington, *The Science and Practice of Pharmacy,* 21st Edition; Lippincott Williams & Wilkins: Philadelphia, Pa., 2005; *Handbook of Pharmaceutical Excipients,* 5th Edition; Rowe et al., ed., The Pharmaceutical Press and the American Pharmaceutical Association: 2005; and *Handbook of Pharmaceutical Additives,* 3rd Edition; Ash and Ash ed., Gower Publishing Company: 2007; *Pharmaceutical Preformulation and Formulation,* Gibson ed., CRC Press LLC: Boca Raton, Fla., 2004.

As used herein, and unless otherwise specified, the term "hydrate" means a compound provided herein or a salt thereof, which further includes a stoichiometric or non-stoichiometric amount of water bound by non-covalent intermolecular forces.

As used herein, and unless otherwise specified, the term "solvate" means a solvate formed from the association of one or more solvent molecules to a compound provided herein. The term "solvate" includes hydrates (e.g., mono-hydrate, dihydrate, trihydrate, tetrahydrate and the like).

As used herein, and unless otherwise specified, a compound described herein is intended to encompass all possible stereoisomers, unless a particular stereochemistry is specified. Where structural isomers of a compound are interconvertible via a low energy barrier, the compound may exist as a single tautomer or a mixture of tautomers. This can take the form of proton tautomerism; or so-called valence tautomerism in the compound, e.g., that contain an aromatic moiety.

As used herein, and unless otherwise specified, a cytidine analog referred to herein is intended to encompass the free base of the cytidine analog, or a salt, solvate, hydrate, cocrystal, complex, prodrug, precursor, metabolite, and/or derivative thereof. In certain embodiments, a cytidine analog referred to herein encompasses the free base of the cytidine analog, or a salt, solvate, hydrate, cocrystal or complex thereof. In certain embodiments, a cytidine analog referred to herein encompasses the free base of the cytidine analog, or a pharmaceutically acceptable salt, solvate, or hydrate thereof.

5.2 Cytidine Analogs

In one embodiment, the methods provided herein comprise administration or co-administration of one or more cytidine analogs. In certain embodiments, the cytidine analog is 5-azacytidine (azacitidine). In certain embodiments, the cytidine analog is 5-aza-2'-deoxycytidine (decitabine). In certain embodiments, the cytidine analog is 5-azacytidine (azacitidine) or 5-aza-2'-deoxycytidine (decitabine). In certain embodiments, the cytidine analog is, for example: 1-β-D-arabinofuranosylcytosine (Cytarabine or ara-C); pseudoisocytidine (psi ICR); 5-fluoro-2'-deoxycytidine (FCdR); 2'-deoxy-2',2'-difluorocytidine (Gemcitabine); 5-aza-2'-deoxy-2',2'-difluorocytidine; 5-aza-2'-deoxy-2'-fluorocytidine; 1-β-D-ribofuranosyl-2(1H)-pyrimidinone (Zebularine); 2',3'-dideoxy-5-fluoro-3'-thiacytidine (Emtriva); 2'-cyclocytidine (Ancitabine); 1-β-D-arabinofuranosyl-5-azacytosine (Fazarabine or ara-AC); 6-azacytidine (6-aza-CR); 5,6-dihydro-5-azacytidine (dH-aza-CR); $N^4$-pentyloxy-carbonyl-5'-deoxy-5-fluorocytidine (Capecitabine); $N^4$-octadecyl-cytarabine; or elaidic acid cytarabine. In certain embodiments, the cytidine analogs provided herein include any compound which is structurally related to cytidine or deoxycytidine and functionally mimics and/or antagonizes the action of cytidine or deoxycytidine.

In certain embodiments, exemplary cytidine analogs have the structures provided below:

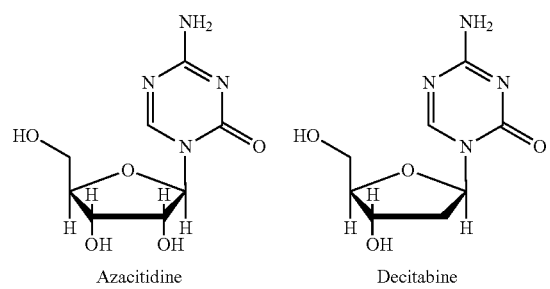

Azacitidine          Decitabine

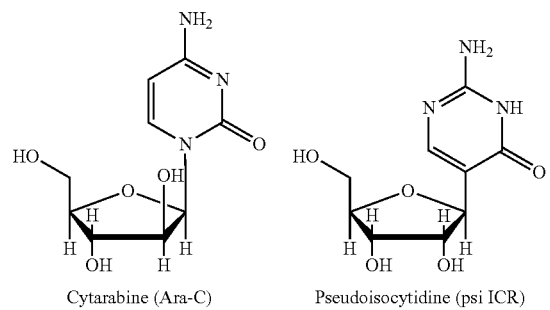

Cytarabine (Ara-C)    Pseudoisocytidine (psi ICR)

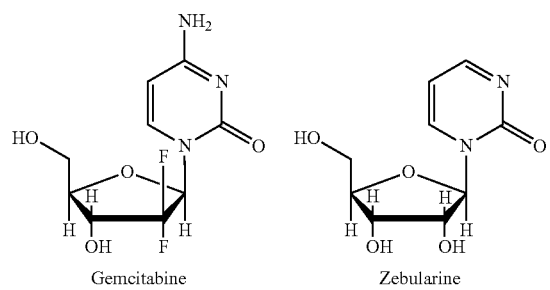

Gemcitabine          Zebularine

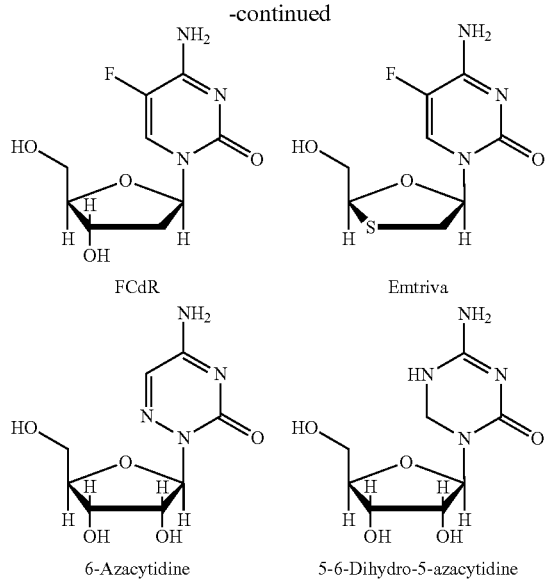

FCdR          Emtriva

6-Azacytidine     5-6-Dihydro-5-azacytidine

Certain embodiments herein provide salts, cocrystals, solvates (e.g., hydrates), complexes, prodrugs, precursors, metabolites, and/or other derivatives of the cytidine analogs provided herein. For example, particular embodiments provide salts, cocrystals, solvates (e.g., hydrates), complexes, precursors, metabolites, and/or other derivatives of 5-azacytidine. Certain embodiments herein provide salts, cocrystals, and/or solvates (e.g., hydrates) of the cytidine analogs provided herein. Certain embodiments herein provide salts and/or solvates (e.g., hydrates) of the cytidine analogs provided herein. Certain embodiments provide cytidine analogs that are not salts, cocrystals, solvates (e.g., hydrates), or complexes of the cytidine analogs provided herein. For example, particular embodiments provide 5-azacytidine in a non-ionized, non-solvated (e.g., anhydrous), non-complexed form. Certain embodiments herein provide a mixture of two or more cytidine analogs provided herein.

Cytidine analogs provided herein may be prepared using synthetic methods and procedures referenced herein or otherwise available in the literature. For example, particular methods for synthesizing 5-azacytidine are disclosed, e.g., in U.S. Pat. No. 7,038,038 and references discussed therein, each of which is incorporated herein by reference. Other cytidine analogs provided herein may be prepared, e.g., using procedures known in the art, or may be purchased from a commercial source.

In one embodiment, the compound used in the methods provided herein is a free base, or a pharmaceutically acceptable salt or solvate thereof. In one embodiment, the free base or the pharmaceutically acceptable salt or solvate is a solid. In another embodiment, the free base or the pharmaceutically acceptable salt or solvate is a solid in an amorphous form. In yet another embodiment, the free base or the pharmaceutically acceptable salt or solvate is a solid in a crystalline form. For example, particular embodiments provide 5-azacytidine in solid forms, which can be prepared, for example, according to the methods described in U.S. Pat. Nos. 6,943,249, 6,887,855 and 7,078,518, and U.S. Patent Application Publication Nos. 2005/027675 and 2006/247189, each of which is incorporated by reference herein in their entireties. In other embodiments, 5-azacytidine in solid forms can be prepared using other methods known in the art.

In one embodiment, the compound used in the methods provided herein is a pharmaceutically acceptable salt of the cytidine analog, which includes, but is not limited to, acetate, adipate, alginate, aspartate, benzoate, benzenesulfonate (besylate), bisulfate, butyrate, citrate, camphorate, camphorsulfonate, cyclopentanepropionate, digluconate, dodecylsulfate, 1,2-ethanedisulfonate (edisylate), ethanesulfonate (esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate (mesylate), 2-naphthalenesulfonate (napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

5.3 Pharmaceutical Compositions

In one embodiment, provided herein are pharmaceutical compositions, which comprise one or more cytidine analogs, or a pharmaceutically acceptable salt or solvate thereof, as an active ingredient, in combination with one or more pharmaceutically acceptable carrier. In one embodiment, the pharmaceutical composition comprises at least one nonrelease controlling excipient or carrier. In one embodiment, the pharmaceutical composition comprises at least one release controlling and at least one nonrelease controlling excipients or carriers.

In certain embodiments, the cytidine analog used in the pharmaceutical compositions provided herein is in a solid form. Suitable solid forms include, but are not limited to, solid forms comprising the free base of the cytidine analog, and solid forms comprising salts of the cytidine analog. In certain embodiments, solid forms provided herein include polymorphs, solvates (including hydrates), and cocrystals comprising the cytidine analog and/or salts thereof. In certain embodiments, the solid form is a crystal form of the cytidine analog, or a pharmaceutically acceptable salt or solvate thereof.

In one embodiment, the pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, e.g., Remington, *The Science and Practice of Pharmacy,* 21st Edition; Lippincott Williams & Wilkins: Philadelphia, Pa., 2005; *Modified-Release Drug Delivery Technology,* Rathbone et al., eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

In one embodiment, the pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

In one embodiment, the pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

5.3.1 Oral Administration

In one embodiment, the pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

In one embodiment, binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pregelatinized starch, and mixtures thereof. The binder or filler may be present from about 50 to about 99% by weight in the pharmaceutical compositions provided herein.

In one embodiment, suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

In one embodiment, suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

In one embodiment, suitable lubricants include, but are not limited to, calcium stearate; magnesium stearate; mineral oil; light mineral oil; glycerin; sorbitol; mannitol; glycols, such as glycerol behenate and polyethylene glycol (PEG) (e.g., PEG400 and PEG6000); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica (silicone dioxide) or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

In one embodiment, suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (e.g., TWEEN® 20), poloxamers (e.g., PLURONIC® F68), polyoxyethylene sorbitan monooleate 80 (e.g., TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, polyvinylpyrrolidone, and lauroyl polyoxylglycerides (e.g., GELUCIRE® 44/14). Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

In one embodiment, suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

It should be understood that many carriers and excipients may serve several functions, even within the same formulation.

In one embodiment, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. In one embodiment, enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. In one embodiment, film coating imparts the same general characteristics as sugar coating. Multiple compressed tablets are compressed tablets made by more than one compression cycle, including layered tablets, and press-coated or dry-coated tablets.

In one embodiment, the tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

In one embodiment, the pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In one embodiment, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

In one embodiment, other useful liquid and semisolid dosage forms include, but are not limited to, those containing the active ingredient(s) provided herein, and a dialkylated monoor poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

In one embodiment, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

In one embodiment, the pharmaceutical compositions provided herein may be formulated as immediate or modified release dosage forms, including delayed-, sustained-, pulsed-, controlled, targeted-, and programmed-release forms.

In one embodiment, the pharmaceutical compositions provided herein may be co-formulated with other active ingredients which do not impair the desired therapeutic action, or with substances that supplement the desired action.

In one embodiment, active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In one embodiment, provided are single unit dosage forms suitable for oral administration such as, but not limited to, tablets, capsules, gelcaps, and caplets that are adapted for controlled-release.

In one embodiment, controlled-release pharmaceutical products improve drug therapy over that achieved by their non-controlled counterparts. In another embodiment, the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another embodiment, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one embodiment, in order to maintain a constant level of drug in the body, the drug can be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.3.2 Parenteral Administration

In one embodiment, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In one embodiment, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., Remington, *The Science and Practice of Pharmacy*, supra).

In one embodiment, the pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

In one embodiment, suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

In one embodiment, suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcellulose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In one embodiment, the pharmaceutical compositions provided herein may be formulated for single or multiple dosage administration. The single dosage formulations are packaged in an ampoule, a vial, or a syringe. The multiple dosage parenteral formulations may contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

In one embodiment, the pharmaceutical compositions provided herein may be formulated as immediate or modified release dosage forms, including delayed-, sustained, pulsed-, controlled, targeted-, and programmed-release forms.

In one embodiment, the pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

In one embodiment, suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

In one embodiment, suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyloxyethanol copolymer, and ethylene/vinyl acetate/vinyl alcohol terpolymer.

5.3.3 Topical Administration

In one embodiment, the pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in, e.g., Remington, *The Science and Practice of Pharmacy*, supra.

In one embodiment, rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

In one embodiment, the pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

In one embodiment, solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

In one embodiment, the pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

In one embodiment, capsules, blisters and cartridges for use in an inhaler or insufflator may be formulated to contain a powder mix of the pharmaceutical compositions provided herein; a suitable powder base, such as lactose or starch; and a performance modifier, such as L-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

In one embodiment, the pharmaceutical compositions provided herein for topical administration may be formulated to be immediate release or modified release, including delayed-, sustained-, pulsed-, controlled-, targeted, and programmed release.

5.3.4 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise one or more second active ingredients as described herein, or a pharmacologically active mutant or derivative thereof, or a combination thereof.

In other embodiments, kits can further comprise devices that are used to administer the active ingredients. Examples of such devices include, but are not limited to, syringes, drip bags, patches, and inhalers.

In one embodiment, kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4 Methods of Use

Provided herein are methods for treating, preventing or managing NSCLC by administering one or more cytidine analogs to a subject having NSCLC. In one embodiment, the methods comprise treating NSCLC with one or more cytidine analogs. In one embodiment, the methods comprise preventing NSCLC with one or more cytidine analogs. In one embodiment, the methods comprise managing NSCLC with one or more cytidine analogs. In certain embodiments, the cytidine analog is 5-azacytidine (azacitidine). In certain embodiments, the cytidine analog is 5-aza-2'-deoxycytidine (decitabine). In certain embodiments, the methods comprise co-administering two or more active agents. In certain embodiments, the subject is a mammal. In certain embodiments, the subject is a human.

In one embodiment, provided herein is use of one or more cytidine analogs (e.g., 5-azacytidine or 5-aza-2'-deoxycytidine) in the manufacture of a medicament for the treatment, prevention, and/or management of NSCLC. In one embodiment, provided herein is use of 5-azacytidine, or a pharmaceutically acceptable salt, solvate, or hydrate thereof, in the manufacture of a medicament for the treatment, prevention, and/or management of NSCLC. In one embodiment, provided herein is use of one or more cytidine analogs (e.g., 5-azacytidine or 5-aza-2'-deoxycytidine) in the manufacture of a medicament for the treatment, prevention, and/or management of a certain type of NSCLC as described herein. In one embodiment, provided herein is use of 5-azacytidine in the manufacture of a medicament for the treatment, prevention, and/or management of a certain type of NSCLC as described herein.

In one embodiment, provided herein is the manufacture of a medicament comprising one or more cytidine analogs (e.g., 5-azacytidine or 5-aza-2'-deoxycytidine) for the treatment, prevention, and/or management of NSCLC. In one embodiment, provided herein is the manufacture of a medicament comprising one or more cytidine analogs (e.g., 5-azacytidine or 5-aza-2'-deoxycytidine) for the treatment, prevention, and/or management of a certain type of NSCLC as described herein. In one embodiment, provided herein is a cytidine analog (e.g., 5-azacytidine or 5-aza-2'-deoxycytidine) for use in the treatment, prevention, and/or management of NSCLC. In one embodiment, provided herein is a cytidine analog (e.g., 5-azacytidine or 5-aza-2'-deoxycytidine) for use in the treatment, prevention, and/or management of a certain type of NSCLC as described herein. In certain embodiments, the cytidine analog is 5-azacytidine (azacitidine). In certain embodiments, the cytidine analog is 5-aza-2'-deoxycytidine (decitabine).

In one embodiment, the methods comprise treating, preventing or managing certain types of NSCLC, including but not limited to, epidermoid or squamous cell carcinoma, large cell carcinoma, adenocarcinoma, adenosquamous carcinoma, carcinomas with pleomorphic, sarcomatoid or sarcomatous elements, carcinoid tumor, carcinomas of salivary-gland, and unclassified carcinoma, by administering one or more cytidine analogs to a subject having NSCLC. In one embodiment, the methods comprise treating, preventing or managing certain types of NSCLC, including but not limited to, epidermoid or squamous cell carcinoma, large cell carcinoma, adenocarcinoma, adenosquamous carcinoma, carcinomas with pleomorphic, sarcomatoid or sarcomatous elements, carcinoid tumor, carcinomas of salivary-gland, and unclassified carcinoma, by administering 5-azacytidine to a subject having NSCLC. In one embodiment, the methods comprise treating, preventing or managing certain types of NSCLC, including but not limited to, epidermoid or squamous cell carcinoma, large cell carcinoma, adenocarcinoma, adenosquamous carcinoma, carcinomas with pleomorphic, sarcomatoid or sarcomatous elements, carcinoid tumor, carcinomas of salivary-gland, and unclassified carcinoma, by administering 5-aza-2'-deoxycytidine to a subject having NSCLC. In one embodiment, the methods comprise the step of identifying in a subject the presence of a certain type of NSCLC. In one embodiment, the methods comprise the step of administering a cytidine analog to a subject having a certain type of NSCLC. In one embodiment, the methods comprise the step of administering 5-azacytidine to a subject having a certain type of NSCLC. In one embodiment, the methods comprise the step of administering 5-aza-2'-deoxycytidine to a subject having a certain type of NSCLC.

In one embodiment, provided herein are methods of treating, preventing or managing certain types of NSCLC, including but not limited to, (1) squamous cell carcinoma, including but not limited to, papillary, clear cell, small cell, and basaloid carcinoma; (2) adenocarcinoma, including but not limited to, acinar, papillary, bronchioloalveolar carcinoma (nonmucinous, mucinous, mixed mucinous and nonmucinous or indeterminate cell type), solid adenocarcinoma with mucin, adenocarcinoma with mixed subtypes, and other variants including well-differentiated fetal adenocarcinoma, mucinous (colloid) adenocarcinoma, mucinous cystadenocarcinoma, signet ring adenocarcinoma, and clear cell adenocarcinoma; (3) large cell carcinoma, including but not limited to, large cell neuroendocrine carcinoma, combined large cell neuroendocrine carcinoma, basaloid carcinoma, lymphoepithelioma-like carcinoma, clear cell carcinoma, and large cell carcinoma with rhabdoid phenotype; (4) adenosquamous carcinoma; (5) carcinomas with pleomorphic, sarcomatoid, or sarcomatous elements, including but not limited to, carcinomas with spindle and/or giant cells, spindle cell carcinoma, giant cell carcinoma, carcinosarcoma, and pulmonary blastoma; (6) carcinoid tumor, including but not limited to, typical carcinoid and atypical carcinoid; (7) carcinomas of salivary-gland, including but not limited to, mucoepidermoid carcinoma and adenoid cystic carcinoma; and (8) unclassified carcinoma; in a subject having NSCLC.

In one embodiment, provided herein are methods of treating, preventing or managing NSCLC by administering one or more cytidine analogs to a subject having NSCLC, wherein the NSCLC is squamous cell carcinoma, including but not limited to, papillary, clear cell, small cell, and basaloid carcinoma. In one embodiment, provided herein are methods of treating, preventing or managing NSCLC by administering 5-azacytidine to a subject having NSCLC, wherein the NSCLC is squamous cell carcinoma, including but not limited to, papillary, clear cell, small cell, and basaloid carcinoma.

In one embodiment, provided herein are methods of treating, preventing or managing NSCLC by administering one or more cytidine analogs to a subject having NSCLC, wherein the NSCLC is adenocarcinoma, including but not limited to, acinar, papillary, bronchioloalveolar carcinoma (nonmucinous, mucinous, mixed mucinous and nonmucinous or indeterminate cell type), solid adenocarcinoma with mucin, adenocarcinoma with mixed subtypes, and other variants including well-differentiated fetal adenocarcinoma, mucinous (colloid) adenocarcinoma, mucinous cystadenocarcinoma, signet ring adenocarcinoma, and clear cell adenocarcinoma. In one embodiment, provided herein are methods of treating, preventing or managing NSCLC by administering 5-azacytidine to a subject having NSCLC, wherein the NSCLC is adenocarcinoma, including but not limited to, acinar, papillary, bronchioloalveolar carcinoma (nonmucinous, mucinous, mixed mucinous and nonmucinous or indeterminate cell type), solid adenocarcinoma with mucin, adenocarcinoma with mixed subtypes, and other variants including well-differentiated fetal adenocarcinoma, mucinous (colloid) adenocarcinoma, mucinous cystadenocarcinoma, signet ring adenocarcinoma, and clear cell adenocarcinoma.

In one embodiment, provided herein are methods of treating, preventing or managing NSCLC by administering one or more cytidine analogs to a subject having NSCLC, wherein the NSCLC is large cell carcinoma, including but not limited to, large cell neuroendocrine carcinoma, combined large cell neuroendocrine carcinoma, basaloid carcinoma, lymphoepithelioma-like carcinoma, clear cell carcinoma, and large cell carcinoma with rhabdoid phenotype. In one embodiment, provided herein are methods of treating, preventing or managing NSCLC by administering 5-azacytidine to a subject having NSCLC, wherein the NSCLC is large cell carcinoma, including but not limited to, large cell neuroendocrine carcinoma, combined large cell neuroendocrine carcinoma, basaloid carcinoma, lymphoepithelioma-like carcinoma, clear cell carcinoma, and large cell carcinoma with rhabdoid phenotype.

In one embodiment, provided herein are methods of treating, preventing or managing NSCLC by administering one or more cytidine analogs to a subject having NSCLC, wherein the NSCLC is adenosquamous carcinoma. In one embodiment, provided herein are methods of treating, preventing or managing NSCLC by administering 5-azacytidine to a subject having NSCLC, wherein the NSCLC is adenosquamous carcinoma.

In one embodiment, provided herein are methods of treating, preventing or managing NSCLC by administering one or more cytidine analogs to a subject having NSCLC, wherein the NSCLC is carcinomas with pleomorphic, sarcomatoid, or sarcomatous elements, including but not limited to, carcinomas with spindle and/or giant cells, spindle cell carcinoma, giant cell carcinoma, carcinosarcoma, and pulmonary blastoma. In one embodiment, provided herein are methods of treating, preventing or managing NSCLC by administering 5-azacytidine to a subject having NSCLC, wherein the NSCLC is carcinomas with pleomorphic, sarcomatoid, or sarcomatous elements, including but not limited to, carcinomas with spindle and/or giant cells, spindle cell carcinoma, giant cell carcinoma, carcinosarcoma, and pulmonary blastoma.

In one embodiment, provided herein are methods of treating, preventing or managing NSCLC by administering one or more cytidine analogs to a subject having NSCLC, wherein the NSCLC is carcinoid tumor, including but not limited to, typical carcinoid and atypical carcinoid. In one embodiment, provided herein are methods of treating, preventing or managing NSCLC by administering 5-azacytidine to a subject having NSCLC, wherein the NSCLC is carcinoid tumor, including but not limited to, typical carcinoid and atypical carcinoid.

In one embodiment, provided herein are methods of treating, preventing or managing NSCLC by administering one or more cytidine analogs to a subject having NSCLC, wherein the NSCLC is carcinomas of salivary-gland, including but not limited to, mucoepidermoid carcinoma and adenoid cystic carcinoma. In one embodiment, provided herein are methods of treating, preventing or managing NSCLC by administering 5-azacytidine to a subject having NSCLC, wherein the NSCLC is carcinomas of salivary-gland, including but not limited to, mucoepidermoid carcinoma and adenoid cystic carcinoma.

In one embodiment, provided herein are methods of treating, preventing or managing NSCLC by administering one or more cytidine analogs to a subject having NSCLC, wherein the NSCLC is unclassified carcinoma. In one embodiment, provided herein are methods of treating, preventing or managing NSCLC by administering 5-azacytidine to a subject having NSCLC, wherein the NSCLC is unclassified carcinoma.

In one embodiment, provided herein are methods of treating, preventing or managing NSCLC in the primary tumor, lymph nodes, and/or distant metastasis, by administering one or more cytidine analogs to a subject having NSCLC. In one embodiment, provided herein are methods of treating, preventing or managing NSCLC in the primary tumor, lymph nodes, and/or distant metastasis, by administering 5-azacytidine to a subject having NSCLC. In one embodiment, provided herein are methods of treating, preventing or managing NSCLC in the primary tumor, lymph nodes, and/or distant metastasis, by administering 5-aza-2'-deoxycytidine to a subject having NSCLC.

In one embodiment, provided herein are methods of treating NSCLC in the primary tumor, by administering one or more cytidine analogs to a subject having NSCLC. In one embodiment, provided herein are methods of treating NSCLC of the primary tumor, by administering 5-azacytidine to a subject having NSCLC. In one embodiment, provided herein are methods of treating NSCLC in the lymph nodes, by administering one or more cytidine analogs to a subject having NSCLC. In one embodiment, provided herein are methods of treating NSCLC in the lymph nodes, by administering 5-azacytidine to a subject having NSCLC. In one embodiment, provided herein are methods of treating NSCLC in distant metastasis, by administering one or more cytidine analogs to a subject having NSCLC. In one embodiment, provided herein are methods of treating NSCLC in distant metastasis, by administering 5-azacytidine to a subject having NSCLC.

In one embodiment, provided herein are methods of treating NSCLC in a subject having surgically resectable NSCLC, locally or regionally advanced NSCLC, and/or distant metastatic NSCLC, by administering one or more cytidine analogs. In one embodiment, provided herein are methods of treating NSCLC in a subject having surgically resectable NSCLC, locally or regionally advanced NSCLC, and/or distant metastatic NSCLC, by administering 5-azacytidine. In one embodiment, provided herein are methods of treating NSCLC in a subject having surgically resectable NSCLC, locally or regionally advanced NSCLC, and/or distant metastatic NSCLC, by administering 5-aza-2'-deoxycytidine.

In one embodiment, provided herein are methods of treating surgically resectable NSCLC, by administering one or more cytidine analogs to a subject having NSCLC. In one embodiment, provided herein are methods of treating surgically resectable NSCLC, by administering 5-azacytidine to a subject having NSCLC. In one embodiment, provided herein are methods of treating locally or regionally advanced NSCLC, by administering one or more cytidine analogs to a subject having NSCLC. In one embodiment, provided herein are methods of treating locally or regionally advanced NSCLC, by administering 5-azacytidine to a subject having NSCLC. In one embodiment, provided herein are methods of treating distant metastatic NSCLC, by administering one or more cytidine analogs to a subject having NSCLC. In one embodiment, provided herein are methods of treating distant metastatic NSCLC, by administering 5-azacytidine to a subject having NSCLC.

In one embodiment, the methods comprise treating, preventing or managing certain stages of NSCLC, including but not limited to, occult carcinoma, Stage 0, Stage IA, Stage IB, Stage IIA, Stage IIB, Stage IIIA, Stage IIIB, and Stage IV, by administering one or more cytidine analogs to a subject having NSCLC. In one embodiment, the methods comprise treating, preventing or managing certain stages of NSCLC, including but not limited to, occult carcinoma, Stage 0, Stage IA, Stage IB, Stage IIA, Stage IIB, Stage IIIA, Stage IIIB, and Stage IIIV, by administering 5-azacytidine to a subject having NSCLC. In one embodiment, the methods comprise treating, preventing or managing certain stages of NSCLC, including but not limited to, occult carcinoma, Stage 0, Stage IA, Stage IB, Stage IIA, Stage IIB, Stage IIIA, Stage IIIB, and Stage IV, by administering 5-aza-2'-deoxycytidine to a subject having NSCLC. The staging of NSCLC may be defined according to methods known in the art, for example, according to the guidelines provided by the American Joint Committee on Cancer (AJCC). In one embodiment, the staging of NSCLC is designated and grouped based on the TNM classification, i.e., a classification based on the status of primary tumor (e.g., TX, T0, Tis, T1, T2, T3, T4), regional lymph nodes (e.g., NX, N0, N1, N2, N3), and/or distant metastasis (e.g., MX, M0, M1), in a subject having NSCLC. See, e.g., Lung in: American Joint Committee on Cancer: AJCC Cancer Staging Manual, 6th ed., New York, N.Y., Springer, 2002, 167-81.

In one embodiment, provided herein are methods for treating subjects having NSCLC, including, e.g., particular NSCLC cell types, using one or more cytidine analogs. In certain embodiments, the cytidine analog is 5-azacytidine (azacitidine). In certain embodiments, the cytidine analog is 5-aza-2'-deoxycytidine (decitabine). In certain embodiments, the methods comprise co-administering with the cytidine analog one or more anticancer agent.

In one embodiment, provided herein are methods for treating certain NSCLC cell types, e.g., those from particular NSCLC cell lines, by administering a cytidine analog (e.g., 5-azacytidine or decitabine). In particular embodiments, NSCLC cell types treated by the methods provided herein include any NSCLC cell type known in the art. In particular embodiments, NSCLC cell types treated by the methods provided herein include, e.g., those from commercially available NSCLC cell lines, such as those available from ATCC®, a commercial cell line repository. Other cell types are known in the art, and include, e.g., those from the cell lines disclosed in Wroblewski et al., Lung Cancer 33:181-94 (2001). Particular NSCLC cell types useful in the methods provided herein include, but are not limited to, A549, H1975, H23, H460, and/or H1299 cells.

Certain embodiments herein provide methods for treating a subject having NSCLC by administering a cytidine analog (e.g., 5-azacytidine). In one embodiment, provided herein are methods comprising the step of identifying in a subject the presence of a particular NSCLC cell type, including but not limited to, A549, H1975, H23, H460, and/or H1299. In one embodiment, provided herein are methods comprising the step of administering a cytidine analog to a subject having a certain NSCLC cell type, including but not limited to, A549, H1975, H23, H460, and/or H1299. In one embodiment, provided herein are methods comprising the step of administering 5-azacytidine to a subject having NSCLC to treat one or more cells of a certain NSCLC cell type, including but not limited to, A549, H1975, H23, H460, and/or H1299. In one embodiment, provided herein are methods comprising the step of contacting a cytidine analog with one or more cells of a certain NSCLC cell type, including but not limited to, A549, H1975, H23, H460, and/or H1299. In one embodiment, provided herein are methods comprising the step of contacting 5-azacytidine with one or more cells of a certain NSCLC cell type, including but not limited to, A549, H1975, H23, H460, and/or H1299. In certain embodiments, the methods may be conducted in vivo, in vitro, and/or ex vivo. In certain embodiments, the methods may be conducted in an animal, e.g., mice or rats. In certain embodiments, the methods provided herein further comprise the step of implanting a certain NSCLC cell type in an animal (e.g., mice or rats) using a method known in the art, followed by the step of treating the animal with one or more cytidine analogs. The time between the implanting step and the treatment step may vary to allow the establishment and/or metastasis of NSCLC in the animal. In certain embodiments, the cells are A549 cells. In certain embodiments, the cells are H1975 cells. In certain embodiments, the cells are H23 cells. In certain embodiments, the cells are H460 cells. In certain embodiments, the cells are H1299 cells.

Certain embodiments herein provide methods for treating a subject having NSCLC by administering a cytidine analog (e.g., 5-azacytidine) to a subject having NSCLC cells having greater sensitivity to AZA than to DAC. In some embodiments, the cells are sensitive to AZA, wherein the $EC_{50}$ of AZA is between about 1 µM and about 10 µM, between about 1 µM and about 6 µM, or between about 1 µM and about 3 µM. In one embodiment, the cells are sensitive to AZA, wherein the $EC_{50}$ of AZA is about 0.1 µM, about 0.3 µM, about 0.5 µM, about 0.7 µM, about 1 µM, about 2 µM, about 3 about 4 µM, about 5 µM, about 6 about 7 µM, about 8 µM, about 9 µM, about 10 µM, or greater than about 10 µM.

In one embodiment, without being limited by a particular theory, the methods provided herein comprise administering a cytidine analog (e.g., 5-azacytidine) to a subject having NSCLC to alter the cell cycle distribution of the subject's NSCLC cells. In one embodiment, without being limited by a particular theory, the methods provided herein comprise contacting a cytidine analog (e.g., 5-azacytidine) with NSCLC cells to alter the cell cycle distribution of the NSCLC cells. In particular embodiments, the cytidine analog (e.g., 5-azacytidine) induces an accumulation of cells in a particular cell cycle phase (e.g., G0, G1, S, G2, and/or M phase). In particular embodiments, the cytidine analog (e.g., 5-azacytidine) induces an accumulation of cells in the sub-G1 cell cycle phase. In particular embodiments, the cytidine analog (e.g., decitabine) induces an accumulation of cells in the G2/M cell cycle phase. In particular embodiments, the DNA cell cycle analysis is performed using a method known in the art, including, e.g., using 4',6-diamidino-2-phenylindole (DAPI) nuclear staining with a flow cytometry apparatus, such as, e.g., one that is commercially available from Beckman Coulter, Fullerton, Calif., USA.

In one embodiment, without being limited by a particular theory, the methods provided herein comprise administering a cytidine analog (e.g., 5-azacytidine) to a subject having NSCLC to alter the rate and/or extent of apoptosis of the subject's NSCLC cells. In one embodiment, without being limited by a particular theory, the methods provided herein comprise contacting a cytidine analog (e.g., 5-azacytidine) with NSCLC cells to alter the rate and/or extent of apoptosis of the NSCLC cells. In particular embodiments, the cytidine analog (e.g., 5-azacytidine) increases the rate and/or extent of apoptosis. In particular embodiments, the rate and/or extent of apoptosis is measured using a method known in the art, including, e.g., AnnexinV staining. Certain embodiments herein provide methods for treating a subject having NSCLC by administering a cytidine analog (e.g., 5-azacytidine) to a subject having NSCLC cells that are positive for AnnexinV staining. In particular embodiments, positive AnnexinV staining is indicative of cells undergoing apoptosis upon exposure to 5-azacytidine.

In one embodiment, without being limited to a particular theory, a possible mechanism of the molecular endpoints obtained in cells treated with cytidine analogs (e.g., 5-azacytidine or 5-aza-2'-deoxycytidine) involves one or more of the following steps: (1) cytidine analogs incorporate into newly synthesized DNA and bind to DNA methyltransferase (DNMT) covalently and irreversibly; (2) trapped DNMTs are degraded in a proteasome-dependent manner; (3) reduced DNMT levels result in DNA hypomethylation; and (4) genes previously silenced by DNA hypermethylation are re-expressed. In one embodiment, without being limited to a particular theory, the re-expression of hypermethylated genes are involved in cell cycle control, cell differentiation, and/or cell apoptosis. In some embodiments, there are controversial data regarding DNMT-dependent versus independent DNA damage signaling via cytidine analog incorporation. See, e.g., Egger et al., *Nature*, 429:457 (2004). In one embodiment, without being limited to a particular theory, a possible mechanism of the molecular endpoints obtained in cells treated with cytidine analogs involves the p95/p21 pathway. In one embodiment, without being limited to a particular theory, a possible mechanism of the molecular endpoints obtained in cells treated with cytidine analogs involves DNA damages.

In some embodiments, without being limited to a particular theory, the mode of action of one cytidine analog (e.g., 5-azacytidine) in the method provided herein differs from that of another cytidine analog (e.g., decitabine). In one embodiment, without being limited to a particular theory, the mode of action of a certain cytidine analog (e.g., 5-azacytidine) in the method provided herein is in addition to, or other than, DNA hypomethylation as described herein. In one embodiment, without being limited to a particular theory, the mode of action of a certain cytidine analog (e.g., 5-azacytidine) in the method provided herein is related to DNA damage, e.g., double-strand DNA breaks. In one embodiment, without being limited to a particular theory, one cytidine analog has a differential effect on NSCLC cell viability than that of another cytidine analog. In one embodiment, without being limited to a particular theory, one cytidine analog has a differential effect on DNA damage in NSCLC cells than that of another cytidine analog. In one embodiment, without being limited to a particular theory, one cytidine analog has a differential effect on NSCLC cell apoptosis than that of another cytidine analog. In one embodiment, without being limited to a particular theory, one cytidine analog has a differential effect on NSCLC cell cycle than that of another cytidine analog. In one embodiment, without being limited to a particular theory, one cytidine analog has a differential effect on gene expression in NSCLC cells than that of another cytidine analog. In one embodiment, the differential effect may be a delay in response to the treatment of cytidine analogs in NSCLC cells, for example, a delay in DNA damage response in certain NSCLC cells. In one embodiment, the differential effect may be the presence or absence of a certain cellular response in NSCLC cells.

In some embodiments, without being limited by a particular theory, pharmacodynamic markers related to the activity of a particular cytidine analog (e.g., 5-azacytidine) include, e.g., one or more of the following: DNMT protein depletion; DNA hypomethylation; DNA damage; cell viability; cell apoptosis; cell cycle control; and gene expression profile. In certain embodiments, the administration of a cytidine analog (e.g., 5-azacytidine or decitabine) to a subject having NSCLC according to a method provided herein depletes DNMT1 protein, e.g., in NSCLC cells. In certain embodiments, the administration of a cytidine analog (e.g., 5-azacytidine) to a subject having NSCLC according to a method provided herein induces DNA hypomethylation, e.g., in NSCLC cells. In particular embodiments, DNMT depletion following administration of a cytidine analog (e.g., 5-azacytidine or decitabine) to a subject having NSCLC indicates DNA incorporation of the cytidine analog. In certain embodiments, the administration of a cytidine analog (e.g., 5-azacytidine) to a subject having NSCLC according to a method provided herein induces markers of DNA damage, e.g., in NSCLC cells. In some embodiments, the DNA damage is double-strand damage. In some embodiments, the DNA damage is single-strand damage. In certain embodiments, the administration of a cytidine analog (e.g., 5-azacytidine) to a subject having NSCLC according to a method provided herein induces markers of cell death, e.g., in NSCLC cells. In certain embodiments, the administration of a cytidine analog (e.g., 5-azacytidine) to a subject having NSCLC according to a method provided herein induces markers of cell viability, e.g., in NSCLC cells. In certain embodiments, the administration of a cytidine analog (e.g., 5-azacytidine) to a subject having NSCLC according to a method provided herein induces markers of cell apoptosis, e.g., in NSCLC cells. In certain embodiments, the administration of a cytidine analog (e.g., 5-azacytidine) to a subject having NSCLC according to a method provided herein induces markers of cell cycle control, e.g., in NSCLC cells. In certain embodiments, the administration of a cytidine analog (e.g., 5-azacytidine) to a subject having NSCLC according to a method provided herein induces markers of differential gene expression, e.g., in NSCLC cells.

In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog depletes DNMT1, e.g., in the subject's NSCLC cells. In one embodiment, the DNMT1 levels are reduced in NSCLC cells when the cells are treated with a cytidine analog at a concentration of less than about 0.001 $\mu$M, about 0.001 $\mu$M, about 0.01 $\mu$M, about 0.03 $\mu$M, about 0.05 $\mu$M, about 0.1 about 0.3 $\mu$M, about 0.5 $\mu$M, about 1 $\mu$M, about 3 $\mu$M, about 5 about 10 $\mu$M, or greater than about 10 $\mu$M.

In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induced DNA hypomethylation, e.g., in the subject's NSCLC cells. In one embodiment, the DNA hypomethylation is measured by examining the methylation status of LINE-1 elements in certain NSCLC cells. In one embodiment, DNA hypomethylation are induced in NSCLC cells when the cells are treated with a cytidine analog at a concentration of less than about 0.001 $\mu$M, about 0.001 $\mu$M, about 0.01 about 0.03 $\mu$M, about 0.05 $\mu$M, about 0.1 $\mu$M, about 0.3 $\mu$M, about 0.5 $\mu$M, about 1 about 3 about 5 about 10 $\mu$M, or greater than about 10 $\mu$M. In one embodiment, peak DNA hypomethylation occurs at concentrations of between about 0.3 $\mu$M and about 1 $\mu$M. In another embodiment, peak DNA hypomethylation occurs at concentrations of about 0.1 $\mu$M.

In some embodiments, without being limited by a particular theory, methods provided herein comprise administering a cytidine analog (e.g., 5-azacytidine) to a subject having NSCLC to induce histone $\gamma$H2AX phosphorylation (a marker of DNA damage), e.g., in NSCLC cells (e.g., A549, H1975, H23, H460, and/or H1299 cells). In one embodiment, histone $\gamma$H2AX (Ser139) phosphorylation is a marker of double-strand DNA breaks. In some embodiments, 5-azacytidine induces histone $\gamma$H2AX phosphorylation in NSCLC cells, e.g., A549, H1975, H23, H460, and/or H1299 cells, to a greater extent than decitabine. In one embodiment, 5-azacytidine induces histone $\gamma$H2AX phosphorylation in NSCLC cells, e.g., A549, H1975, H23, H460, and/or H1299 cells, at an earlier time point than decitabine. In one embodiment, 5-azacytidine induces double-strand DNA breaks. In one embodiment, decitabine induces single-strand DNA breaks.

In some embodiments, without being limited by a particular theory, methods provided herein comprise administering a cytidine analog (e.g., 5-azacytidine) to a subject having NSCLC to induce PARP cleavage (a marker of cell death), e.g., in NSCLC cells (e.g., A549, H1975, H23, H460, and/or H1299 cells). In particular embodiments, 5-azacytidine induces PARP cleavage in NSCLC cells, e.g., A549, H1975, H23, H460, and/or H1299 cells, to a greater extent than decitabine.

In some embodiments, without being limited by a particular theory, methods provided herein comprise administering a cytidine analog (e.g., 5-azacytidine) to a subject having NSCLC to induce Caspase-3 cleavage (a marker of cell death), e.g., in NSCLC cells (e.g., A549, H1975, H23, H460, and/or H1299 cells). In particular embodiments, 5-azacytidine induces PARP cleavage in NSCLC cells, e.g., A549, H1975, H23, H460, and/or H1299 cells, to a greater extent than decitabine.

In some embodiments, without being limited by a particular theory, methods provided herein comprise administering a cytidine analog (e.g., 5-azacytidine) to a subject having NSCLC to render cells positive for AnnexinV staining (a marker for apoptosis), e.g., in NSCLC cells (e.g., A549, H1975, H23, H460, and/or H1299 cells). In one embodiment, AnnexinV staining is a marker for early apoptosis (e.g., AnnexinV-FITC$^+$ and 7-AAD$^-$). In one embodiment, AnnexinV staining is a marker for late apoptosis (e.g., AnnexinV-FITC$^+$ and 7-AAD$^+$). In particular embodiments, 5-azacytidine results in positive AnnexinV staining in NSCLC cells, e.g., A549, H1975, H23, H460, and/or H1299 cells, to a greater extent than decitabine. In particular embodiment, 5-azacytidine induces an increase in the early- and/or late-apoptotic populations in NSCLC cells, e.g., A549, H1975, H23, H460, and/or H1299 cells.

In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induces cell death (i.e., not just cell cycle arrest).

In one embodiment, without being limited by a particular theory, provided herein are methods for treating a subject having NSCLC by administering a cytidine analog (e.g., 5-azacytidine) to a subject to achieve a different gene expression profile in one or more of the subject's NSCLC cell types than one could achieve by administering a different cytidine analog (e.g., decitabine). In one embodiment, gene expression is assessed by microarray analysis. In one embodiment, certain gene expressions are induced in NSCLC cells when the cells are treated with a cytidine analog at a concentration of about 0.001 $\mu$M, about 0.01 $\mu$M, about 0.03 $\mu$M, about 0.05 $\mu$M, about 0.1 $\mu$M, about 0.3 $\mu$M, about 0.5 $\mu$M about 1 $\mu$M, about 3 $\mu$M, about 5 $\mu$M, about 10 $\mu$M, or greater than about 10 $\mu$M. In one embodiment, certain gene expressions are induced in NSCLC cells when the cells are treated with a cytidine analog at a concentration of between about 0.3 $\mu$M and about 3 $\mu$M. In one embodiment, certain gene expressions are induced in NSCLC cells when the cells are treated with a cytidine analog at a concentration of between about 1 $\mu$M and about 3 $\mu$M. In one embodiment, without being limited by a particular theory, 5-azacytidine induces upregulation of genes associated with response to DNA damage stimulus and/or DNA repair, e.g., in NSCLC cells (e.g., A549, H1975, H23, H460, and/or H1299 cells). In one embodiment, without being limited by a particular theory, decitabine induces down-regulation of genes associated with response to DNA damage stimulus and/or DNA repair, e.g., in NSCLC cells (e.g., A549, H1975, H23, H460, and/or H1299 cells).

In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induces DNA hypomethylation in RAS association domain family protein (RASSF1A) gene, e.g., in the subject's NSCLC cells. In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induces DNA hypomethylation in adenomatous polyposis coli (APC) gene, e.g., in the subject's NSCLC cells. In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induces DNA hypomethylation in fragile histidine triad (FHIT) gene, e.g., in the subject's NSCLC cells. In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog induces DNA hypomethylation in $p16^{INK4A}$ gene, e.g., in the subject's NSCLC cells.

In some embodiments, methods provided herein comprise administering a cytidine analog (e.g., 5-azacytidine) to a subject having NSCLC (e.g., comprising a cell type selected from A549, H1975, H23, H460, and H1299), wherein the cytidine analog (e.g., 5-azacytidine) induces DNA damage and/or cell death at a lower concentration than another cytidine analog. In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog (e.g., 5-azacytidine) modulates the expression of a greater number of genes than another cytidine analog at the same concentration (e.g., about 0.3 µM, about 1 µM, or about 3 µM).

In some embodiments, without being limited by a particular theory, methods provided herein comprise administering a cytidine analog (e.g., 5-azacytidine) to a subject having NSCLC (e.g., comprising a cell type selected from A549, H1975, H23, H460, and H1299), wherein the cytidine analog (e.g., 5-azacytidine) has additional effects via RNA incorporation. In one embodiment, without being limited by a particular theory, the effects of RNA incorporation are (1) alterations in the synthesis and processing of various species of RNA, (2) inhibition of transcription, and/or (3) disruption of protein synthesis.

In some embodiments, methods provided herein comprise administering a cytidine analog (e.g., 5-azacytidine) to a subject having NSCLC (e.g., comprising a cell type selected from A549, H1975, H23, H460, and H1299), wherein the cytidine analog (e.g., 5-azacytidine) achieves higher plasma levels than another cytidine analog (e.g., decitabine). For example, in particular embodiments, VIDAZA® adminis-tered at 75 mg/m² achieves plasma levels of 3 µM, whereas DACOGEN® administered at 15 mg/m² achieves plasma levels of 0.5 µM.

In particular embodiments, methods provided herein comprise administering a cytidine analog to a subject having a NSCLC tumor that is surgically resectable. In particular embodiments, the methods provided herein comprise administering a cytidine analog to a subject having locally advanced NSCLC. In particular embodiments, methods provided herein comprise administering a cytidine analog to a subject having regionally advanced NSCLC. In particular embodiments, the methods provided herein comprise administering a cytidine analog to a subject having a distant metastasis, e.g., at the time of diagnosis.

Particular embodiments provide treating a subject having NSCLC using one or more of the methods provided herein, together with surgery. Particular embodiments provide treating a subject having NSCLC using one or more of the methods provided herein, together with chemotherapy. Particular embodiments provide treating a subject having NSCLC using one or more of the methods provided herein, together with immunotherapy. Particular embodiments provide treating a subject having NSCLC using one or more of the methods provided herein, together with targeted therapy. Particular embodiments provide treating a subject having NSCLC using one or more of the methods provided herein, together with radiation therapy. Particular embodiments provide treating a subject having NSCLC using one or more of the methods provided herein, together with two or more of the treatments selected from surgery, chemotherapy, immunotherapy, targeted therapy, and radiation therapy. Particular embodiments provide treating a subject having NSCLC using one or more of the methods provided herein, together with two or more of the treatments selected from surgery, chemotherapy, and radiation therapy.

In certain embodiments, the subject to be treated with one of the methods provided herein has not been treated with anticancer therapy prior to the administration of the cytidine analog. In certain embodiments, the subject to be treated with one of the methods provided herein has been treated with one or more anticancer therapies prior to the administration of the cytidine analog. In certain embodiments, the subject to be treated with one of the methods provided herein has been treated with a cancer therapeutic agent, as described herein. In certain embodiments, the subject to be treated with one of the methods provided herein has developed drug resistance to anticancer therapy. In certain embodiments, the subject to be treated with the methods provided herein has a relapsed cancer. In certain embodiments, the subject to be treated with the methods provided herein has a refractory cancer. In certain embodiments, the subject to be treated with the methods provided herein has a metastatic cancer.

In one embodiment, the methods provided herein encompass treating a subject regardless of patient's age, although some diseases or disorders are more common in certain age groups. Further provided herein is a method for treating a subject who has undergone surgery in an attempt to treat the disease or condition at issue. Further provided herein is a method for treating a subject who has not undergone surgery as an attempt to treat the disease or condition at issue. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

In each embodiment provided herein, the method may further comprise one or more diagnostic steps, to determine, e.g., the type of NSCLC, the presence of particular cell types, and/or the staging of the disease in a subject.

In each embodiment provided herein, the method may further comprise a disease evaluation step after the cytidine analog has been administered to the subject, to determine, e.g., changes in one or more molecular markers as described herein elsewhere, changes in tumor size and location, and/or other benchmarks used by those skilled in the art to determine the prognosis of NSCLC in a subject.

5.4.1 Administration of Cytidine Analogs

Certain methods herein provide administration of the cytidine analog by, e.g., intravenous (IV), subcutaneous (SC) or oral routes administration. Certain embodiments herein provide co-administration of a cytidine analog (e.g., 5-azacytidine) with one or more additional active agents to provide a synergistic therapeutic effect in subjects in need thereof. The co-administered agent(s) may be a cancer therapeutic agent, as described herein. In certain embodiments, the co-administered agent(s) may be dosed, e.g., orally or by injection (e.g., IV or SC).

Certain embodiments herein provide methods for treating disorders of abnormal cell proliferation comprising administering a cytidine analog using, e.g., IV, SC and/or oral administration methods. In certain embodiments, treatment cycles comprise multiple doses administered to a subject in need thereof over multiple days (e.g., 1, 2, 3, 4, 5, 6, 7, 8, 9, 10, 11, 12, 13, 14, or greater than 14 days), optionally followed by treatment dosing holidays (e.g., 1, 2, 3, 4, 5, 6, 7, 8, 9, 10, 11, 12, 13, 14, or greater than 14 days). Suitable dosage amounts for the methods provided herein include, e.g., therapeutically effective amounts and prophylactically effective amounts. For example, in certain embodiments, the amount of the cytidine analog (e.g., 5-azacytidine) administered in the methods provided herein may range, e.g., between about 50 mg/m$^2$/day and about 2,000 mg/m$^2$/day, between about 100 mg/m$^2$/day and about 1,000 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day. In certain embodiments, particular dosages are, e.g., up to about 120 mg/m$^2$/day, up to about 140 mg/m$^2$/day, up to about 150 mg/m$^2$/day, up to about 180 mg/m$^2$/day, up to about 200 mg/m$^2$/day, up to about 220 mg/m$^2$/day, up to about 240 mg/m$^2$/day, up to about 250 mg/m$^2$/day, up to about 260 mg/m$^2$/day, up to about 280 mg/m$^2$/day, up to about 300 mg/m$^2$/day, up to about 320 mg/m$^2$/day, up to about 350 mg/m$^2$/day, up to about 380 mg/m$^2$/day, up to about 400 mg/m$^2$/day, up to about 450 mg/m$^2$/day, up to about 500 mg/m$^2$/day, up to about 750 mg/m$^2$/day, or up to about 1000 mg/m$^2$/day.

In one embodiment, the amount of the cytidine analog (e.g., 5-azacytidine) administered in the methods provided herein may range, e.g., between about 5 mg/day and about 2,000 mg/day, between about 10 mg/day and about 2,000 mg/day, between about 20 mg/day and about 2,000 mg/day, between about 50 mg/day and about 1,000 mg/day, between about 100 mg/day and about 500 mg/day, between about 150 mg/day and about 500 mg/day, or between about 150 mg/day and about 250 mg/day. In certain embodiments, particular dosages are, e.g., about 10 mg/day, about 20 mg/day, about 50 mg/day, about 75 mg/day, about 100 mg/day, about 120 mg/day, about 150 mg/day, about 200 mg/day, about 250 mg/day, about 300 mg/day, about 350 mg/day, about 400 mg/day, about 450 mg/day, about 500 mg/day, about 600 mg/day, about 700 mg/day, about 800 mg/day, about 900 mg/day, about 1,000 mg/day, about 1,200 mg/day, or about 1,500 mg/day. In certain embodiments, particular dosages are, e.g., up to about 10 mg/day, up to about 20 mg/day, up to about 50 mg/day, up to about 75 mg/day, up to about 100 mg/day, up to about 120 mg/day, up to about 150 mg/day, up to about 200 mg/day, up to about 250 mg/day, up to about 300 mg/day, up to about 350 mg/day, up to about 400 mg/day, up to about 450 mg/day, up to about 500 mg/day, up to about 600 mg/day, up to about 700 mg/day, up to about 800 mg/day, up to about 900 mg/day, up to about 1,000 mg/day, up to about 1,200 mg/day, or up to about 1,500 mg/day.

In one embodiment, the amount of the cytidine analog (e.g., 5-azacytidine) in the pharmaceutical composition or dosage form provided herein may range, e.g., between about 5 mg and about 2,000 mg, between about 10 mg and about 2,000 mg, between about 20 mg and about 2,000 mg, between about 50 mg and about 1,000 mg, between about 100 mg and about 500 mg, between about 150 mg and about 500 mg, or between about 150 mg and about 250 mg. In certain embodiments, particular amounts are, e.g., about 10 mg, about 20 mg, about 50 mg, about 75 mg, about 100 mg, about 120 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1,000 mg, about 1,200 mg, or about 1,500 mg. In certain embodiments, particular amounts are, e.g., up to about 10 mg, up to about 20 mg, up to about 50 mg, up to about 75 mg, up to about 100 mg, up to about 120 mg, up to about 150 mg, up to about 200 mg, up to about 250 mg, up to about 300 mg, up to about 350 mg, up to about 400 mg, up to about 450 mg, up to about 500 mg, up to about 600 mg, up to about 700 mg, up to about 800 mg, up to about 900 mg, up to about 1,000 mg, up to about 1,200 mg, or up to about 1,500 mg.

In one embodiment, depending on the disease to be treated and the subject's condition, the cytidine analog (e.g., 5-azacytidine) may be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. The cytidine analog may be formulated, alone or together with one or more active agent(s), in suitable dosage unit with pharmaceutically acceptable excipients, carriers, adjuvants and vehicles, appropriate for each route of administration. In one embodiment, the cytidine analog (e.g., 5-azacytidine) is administered orally. In another embodiment, the cytidine analog (e.g., 5-azacytidine) is administered parenterally. In yet another embodiment, the cytidine analog (e.g., 5-azacytidine) is administered intravenously.

In one embodiment, the cytidine analog (e.g., 5-azacytidine) can be delivered as a single dose such as, e.g., a single bolus injection, or oral tablets or pills; or over time such as, e.g., continuous infusion over time or divided bolus doses over time. In one embodiment, the cytidine analog (e.g., 5-azacytidine) can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. See, e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient's symptoms, physical examination, visualization of the tumor that has been imaged using X-ray, CAT, PET, or MRI scan and other commonly accepted evaluation modalities.

In one embodiment, the cytidine analog (e.g., 5-azacytidine) can be administered once daily (QD), or divided into multiple daily doses such as twice daily (BID), three times daily (TID), and four times daily (QID). In one embodiment, the administration can be continuous (i.e., daily for consecutive days or every day), intermittent, e.g., in cycles (i.e., including days, weeks, or months of rest when no drug is administered). In one embodiment, the cytidine analog (e.g., 5-azacytidine) is administered daily, for example, once or more than once each day for a period of time. In one embodiment, the cytidine analog (e.g., 5-azacytidine) is administered daily for an uninterrupted period of at least 7 days, in some embodiments, up to 52 weeks. In one embodiment, the cytidine analog (e.g., 5-azacytidine) is administered intermittently, i.e., stopping and starting at either regular or irregular intervals. In one embodiment, the cytidine analog (e.g., 5-azacytidine) is administered for one to six days per week. In one embodiment, the cytidine analog (e.g., 5-azacytidine) is administered in cycles (e.g., daily administration for two to eight consecutive weeks, then a rest period with no administration for up to one week). In one embodiment, the cytidine analog (e.g., 5-azacytidine) is administered on alternate days. In one embodiment, the cytidine analog (e.g., 5-azacytidine) is administered in cycles (e.g., administered daily or continuously for a certain period interrupted with a rest period).

In one embodiment, the frequency of administration ranges from about daily to about monthly. In certain embodiments, the cytidine analog (e.g., 5-azacytidine) is administered once a day, twice a day, three times a day, four times a day, once every other day, twice a week, once every week, once every two weeks, once every three weeks, or once every four weeks. In one embodiment, the cytidine analog (e.g., 5-azacytidine) is administered once a day. In another embodiment, the cytidine analog (e.g., 5-azacytidine) is administered twice a day. In yet another embodiment, the cytidine analog (e.g., 5-azacytidine) is administered three times a day. In still another embodiment, the cytidine analog (e.g., 5-azacytidine) is administered four times a day.

In one embodiment, the cytidine analog (e.g., 5-azacytidine) is administered once per day from one day to six months, from one week to three months, from one week to four weeks, from one week to three weeks, or from one week to two weeks. In certain embodiments, the cytidine analog (e.g., 5-azacytidine) is administered once per day for one week, two weeks, three weeks, or four weeks. In one embodiment, the cytidine analog (e.g., 5-azacytidine) is administered once per day for one week. In another embodiment, the cytidine analog (e.g., 5-azacytidine) is administered once per day for two weeks. In yet another embodiment, the cytidine analog (e.g., 5-azacytidine) is administered once per day for three weeks. In still another embodiment, the cytidine analog (e.g., 5-azacytidine) is administered once per day for four weeks.

In one embodiment, the cytidine analog (e.g., 5-azacytidine) is administered once per day for about 1 week, about 2 weeks, about 3 weeks, about 4 weeks, about 6 weeks, about 9 weeks, about 12 weeks, about 15 weeks, about 18 weeks, about 21 weeks, or about 26 weeks. In certain embodiments, the cytidine analog (e.g., 5-azacytidine) is administered intermittently. In certain embodiments, the cytidine analog (e.g., 5-azacytidine) is administered intermittently in the amount of between about 50 mg/m$^2$/day and about 2,000 mg/m$^2$/day. In certain embodiments, the cytidine analog (e.g., 5-azacytidine) is administered continuously. In certain embodiments, the cytidine analog (e.g., 5-azacytidine) is administered continuously in the amount of between about 50 mg/m$^2$/day and about 1,000 mg/m$^2$/day.

In certain embodiments, the cytidine analog (e.g., 5-azacytidine) is administered to a patient in cycles. Cycling therapy involves the administration of an active agent for a period of time, followed by a rest for a period of time, and repeating this sequential administration. Cycling therapy can reduce the development of resistance, avoid or reduce the side effects, and/or improves the efficacy of the treatment.

Accordingly, in one embodiment, the cytidine analog (e.g., 5-azacytidine) is administered daily in single or divided doses for about one week, about two weeks, about three weeks, about four weeks, about five weeks, about six weeks, about eight weeks, about ten weeks, about fifteen weeks, or about twenty weeks, followed by a rest period of about 1 day to about ten weeks. In one embodiment, the methods provided herein contemplate cycling treatments of about one week, about two weeks, about three weeks, about four weeks, about five weeks, about six weeks, about eight weeks, about ten weeks, about fifteen weeks, or about twenty weeks. In some embodiments, the cytidine analog (e.g., 5-azacytidine) is administered daily in single or divided doses for about one week, about two weeks, about three weeks, about four weeks, about five weeks, or about six weeks with a rest period of about 1, 3, 5, 7, 9, 12, 14, 16, 18, 20, 22, 24, 26, 28, 29, or 30 days. In some embodiments, the rest period is 1 day. In some embodiments, the rest period is 3 days. In some embodiments, the rest period is 7 days. In some embodiments, the rest period is 14 days. In some embodiments, the rest period is 28 days. The frequency, number and length of dosing cycles can be increased or decreased.

In one embodiment, the methods provided herein comprise: i) administering to the subject a first daily dose of the cytidine analog (e.g., 5-azacytidine); ii) optionally resting for a period of at least one day where the cytidine analog (e.g., 5-azacytidine) is not administered to the subject; iii) administering a second dose of the cytidine analog (e.g., 5-azacytidine) to the subject; and iv) repeating steps ii) to iii) a plurality of times. In certain embodiments, the first daily dose is between about 50 mg/m$^2$/day and about 2,000 mg/m$^2$/day. In certain embodiments, the second daily dose is between about 50 mg/m$^2$/day and about 2,000 mg/m$^2$/day. In certain embodiments, the first daily dose is higher than the second daily dose. In certain embodiments, the second daily dose is higher than the first daily dose. In one embodiment, the rest period is 2 days, 3 days, 5 days, 7 days, 10 days, 12 days, 13 days, 14 days, 15 days, 17 days, 21 days, or 28 days. In one embodiment, the rest period is at least 2 days and steps ii) through iii) are repeated at least three times. In one embodiment, the rest period is at least 2 days and steps ii) through iii) are repeated at least five times. In one embodiment, the rest period is at least 3 days and steps ii) through iii) are repeated at least three times. In one embodiment, the rest period is at least 3 days and steps ii) through iii) are repeated at least five times. In one embodiment, the rest period is at least 7 days and steps ii) through iii) are repeated at least three times. In one embodiment, the rest period is at least 7 days and steps ii) through iii) are repeated at least five times. In one embodiment, the rest period is at least 14 days and steps ii) through iii) are repeated at least three times. In one embodiment, the rest period is at least 14 days and steps ii) through iii) are repeated at least five times. In one embodiment, the rest period is at least 21 days and steps ii) through iii) are repeated at least three times. In one embodiment, the rest period is at least 21 days and steps ii) through iii) are repeated at least five times. In one embodiment, the rest period is at least 28 days and steps ii) through iii) are repeated at least three times. In one embodiment, the rest period is at least 28 days and steps ii) through iii) are repeated at least five times.

In certain embodiments, the cytidine analog (e.g., 5-azacytidine) is administered continuously for between about 1 and about 52 weeks. In certain embodiments, the cytidine analog (e.g., 5-azacytidine) is administered continuously for about 1, 2, 3, 4, 5, 6, 7, 8, 9, 10, 11, or 12 months. In certain embodiments, the cytidine analog (e.g., 5-azacytidine) is administered continuously for about 14, about 28, about 42, about 84, or about 112 days. It is understood that the duration of the treatment may vary with the age, weight, and condition of the subject being treated, and may be determined empirically using known testing protocols or according to the professional judgment of the person providing or supervising the treatment. The skilled clinician will be able to readily determine, without undue experimentation, an effective drug dose and treatment duration, for treating an individual subject having a particular type of cancer.

5.4.2 Co-Administered Therapeutic Agents

In certain embodiments, methods provided herein for treating NSCLC comprise co-administering a cytidine analog, such as, for example, 5-azacytidine, with one or more therapeutic agents, such as, for example, cancer therapeutic agents, to yield a synergistic therapeutic effect. The co-administered therapeutic agents include, but are not limited to, e.g., cytotoxic agents, anti-metabolites, antifolates, HDAC inhibitors such as MGCD0103 (a.k.a. N-(2-aminophenyl)-4-((4-(pyridin-3-yl)pyrimidin-2-ylamino)methyl)benzamide), DNA intercalating agents, DNA cross-linking agents, DNA alkylating agents, DNA cleaving agents, topoisomerase inhibitors, CDK inhibitors, JAK inhibitors, anti-angiogenic agents, Bcr-Abl inhibitors, HER2 inhibitors, EGFR inhibitors, VEGFR inhibitors, PDGFR inhibitors, HGFR inhibitors, IGFR inhibitors, c-Kit inhibitors, Ras pathway inhibitors, PI3K inhibitors, multi-targeted kinase inhibitors, mTOR inhibitors, anti-estrogens, anti-androgens, aromatase inhibitors, somatostatin analogs, ER modulators, anti-tubulin agents, vinca alkaloids, taxanes, HSP inhibitors, Smoothened antagonists, telomerase inhibitors, COX-2 inhibitors, anti-metastatic agents, immunosuppressants, biologics such as antibodies, and hormonal therapies. In particular embodiment, the co-administered therapeutic agent is thalidomide, lenalidomide, or pomalidomide. The co-administered agent may be dosed, e.g., orally or by injection.

In one embodiment, the route of the administration of the cytidine analog (e.g., 5-azacytidine) is independent of the route of the administration of a second therapy. In one embodiment, the cytidine analog (e.g., 5-azacytidine) is administered orally. In another embodiment, the cytidine analog (e.g., 5-azacytidine) is administered intravenously. In accordance with these embodiments, the cytidine analog (e.g., 5-azacytidine) is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraocularly, via local delivery by catheter or stent, subcutaneously, intraadiposally, intraarticularly, intrathecally, or in a slow release dosage form. In one embodiment, the cytidine analog (e.g., 5-azacytidine) and a second therapy are administered by the same mode of administration, e.g., orally or intravenously. In another embodiment, the cytidine analog (e.g., 5-azacytidine) is administered by one mode of administration, e.g., intravenously, whereas the second agent (e.g., an anticancer agent) is administered by another mode of administration, e.g., orally. In another embodiment, the cytidine analog (e.g., 5-azacytidine) is administered by one mode of administration, e.g., orally, whereas the second agent (e.g., an anticancer agent) is administered by another mode of administration, e.g., intravenously.

In one embodiment, each method provided herein may independently, further comprise the step of administering a second therapeutic agent. In one embodiment, the second therapeutic agent is an anticancer agent. In one embodiment, the anticancer agent is an antimetabolite, including, but not limited to, 5-fluoro uracil, methotrexate, cytarabine, high dose cytarabine, and fludarabine. In one embodiment, the anticancer agent is an antimicrotubule agent, including, but not limited to, vinca alkaloids (e.g., vincristine and vinblastine) and taxanes (e.g., paclitaxel and docetaxel). In one embodiment, the anticancer agent is an alkylating agent, including, but not limited to, cyclophosphamide, melphalan, carmustine, and nitrosoureas (e.g., hydroxyurea and bischloroethylnitrosurea). In one embodiment, the anticancer agent is a platinum agent, including, but not limited to, cisplatin, carboplatin, oxaliplatin, satraplatin (JM-216), and CI-973. In one embodiment, the anticancer agent is an anthracycline, including, but not limited to, doxrubicin and daunorubicin. In one embodiment, the anticancer agent is an antitumor antibiotic, including, but not limited to, mitomycin, idarubicin, adriamycin, and daunomycin (also known as daunorubicin). In one embodiment, the anticancer agent is a topoisomerase inhibitor, e.g., etoposide and camptothecins. In one embodiment, the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

In one embodiment, other therapies or anticancer agents that may be used in combination with the cytidine analog (e.g., 5-azacytidine) include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, and ifosfamide), antimetabolites (cytarabine, high dose cytarabine, and methotrexate), purine antagonists and pyrimidine antagonists (6-mercaptopurine, 5-fluorouracil, cytarabine, and gemcitabine), spindle poisons (vinblastine, vincristine, vinorelbine, and paclitaxel), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For additional available cancer therapies, see, e.g., http://www.nci.nih.gov/; for a list of FDA approved oncology drugs, see, e.g., http://www.fda.gov/, The Merck Manual, 18th Ed. 2006, and PDR: Physician Desk Reference 2010, 64th Ed. 2009; the contents of each of which are hereby incorporated by reference in their entireties.

5.4.3 Biomarkers

In certain embodiments, appropriate biomarkers may be used to determine or predict the effect of the methods provided herein on the disease state and to provide guidance as to the dosing schedule. For example, particular embodiments herein provide a method for determining whether a patient diagnosed with NSCLC has an increased probability of obtaining a greater benefit from treatment with a pharmaceutical composition comprising a cytidine analog by assessing the patient's nucleic acid methylation status. In particular embodiments, the cytidine analog is 5-azacytidine. In particular embodiments, the nucleic acid is DNA or RNA. In particular embodiments, the greater benefit is an overall survival benefit. In particular embodiments, the methylation status is examined in one or more genes, e.g., genes associated with NSCLC. Specific embodiments involve methods for determining whether baseline DNA methylation levels influence overall survival in patients with NSCLC treated with 5-azacytidine. Specific embodiments provide methods for determining whether gene promoter methylation levels influence overall survival in patients with NSCLC.

In one embodiment, provided herein is a method for determining whether a patient diagnosed with NSCLC has an increased probability of obtaining a greater benefit from treatment with a pharmaceutical composition comprising a cytidine analog by assessing the gene expression profile in the patient. In one embodiment, provided herein is a method for determining whether a patient diagnosed with NSCLC has an increased probability of obtaining a greater benefit from treatment with a pharmaceutical composition comprising a cytidine analog by assessing molecular markers, including one or more cell cycle markers, apoptosis markers, and DNA damage markers. In one embodiment, provided herein is a method for determining whether a patient diagnosed with NSCLC has increased probability of obtaining a greater benefit from treatment with a pharmaceutical composition comprising a cytidine analog by assessing phosphorylation of Histone H2AX (marker of DNA damage) and cleavage of PARP (marker of apoptosis). In particular embodiments, the cytidine analog is 5-azacytidine. In particular embodiments, the greater benefit is an overall survival benefit.

VI. EXAMPLES

6.1 Example 1

Figure 2:
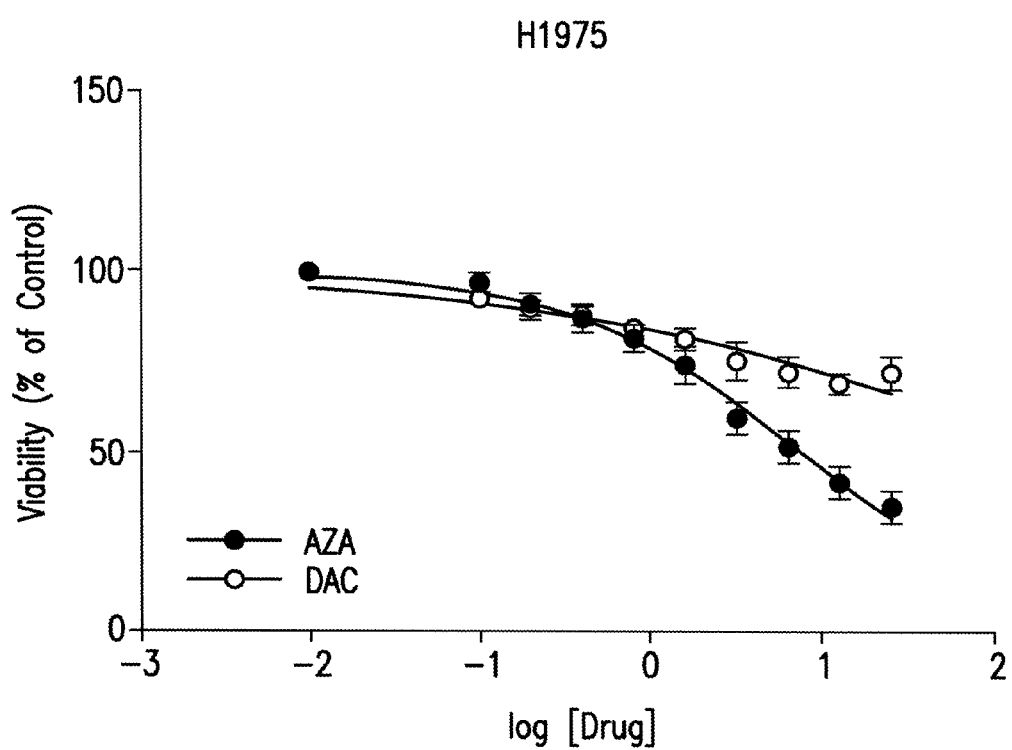
FIG. 2 represents effects of AZA and DAC on the viability of H1975 cells.
Figure 3:
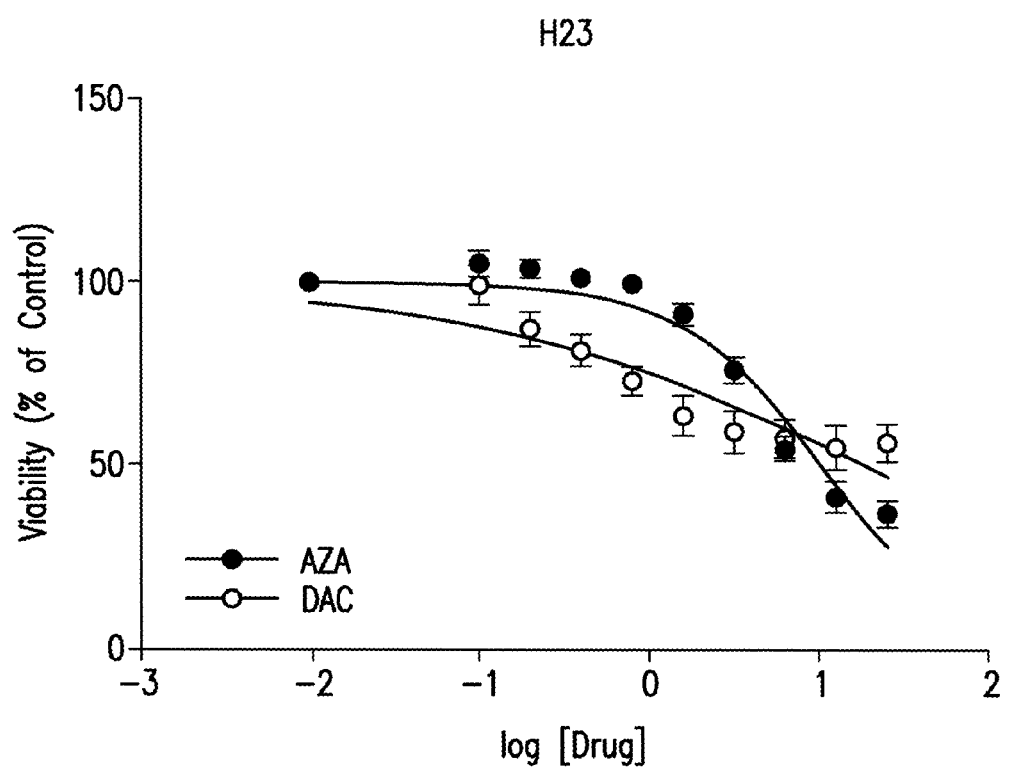
FIG. 3 represents effects of AZA and DAC on the viability of H23 cells.
Figure 4:
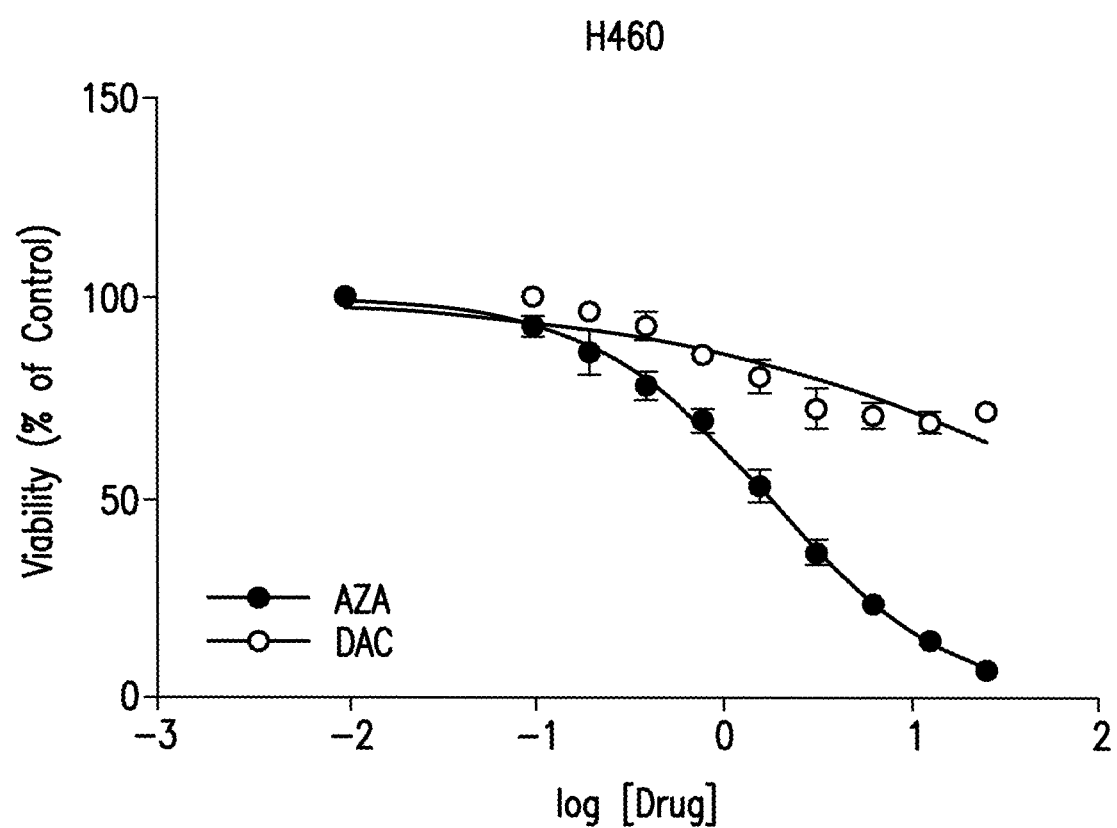
FIG. 4 represents effects of AZA and DAC on the viability of H460 cells.
Figure 5:
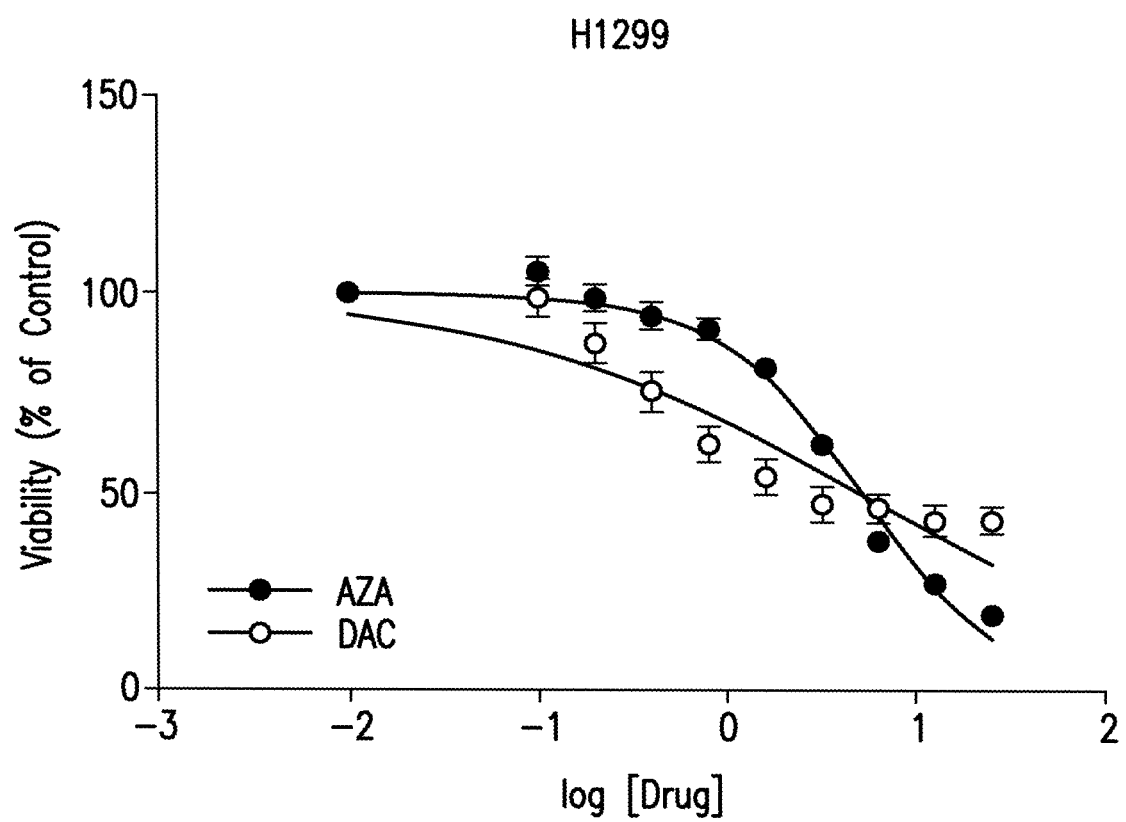
FIG. 5 represents effects of AZA and DAC on the viability of H1299 cells.

Studies were performed to determine the effects of azacitidine (AZA) and decitabine (DAC) on the viability of particular NSCLC cell types. The following six cell lines were examined: A549 (Table 1 and FIG. 1), H1975 (Table 2 and FIG. 2), H23 (Table 3 and FIG. 3), H460 (Table 4 and FIG. 4), and H1299 (Table 5 and FIG. 5).

Certain NSCLC cell lines (H460, H1299, A549, and H1975) were purchased from American Type Culture Collection (ATCC; Manassas, Va.). The $H_{23}$NSCLC cell line was obtained from the National Cancer Institute (NCI; Bethesda, Md.). Cell lines were cultured in their respective media, as recommended by ATCC and NCI. AZA was manufactured at Aptuit (Greenwich, Conn.) for Celgene (Summit, N.J.), while DAC was purchased from Sigma-Aldrich (St. Louis, Mo.). In all experiments, cells were seeded 24 hours before drug treatment and incubated at 37° C./5% $CO_2$. For cell viability assays, H460, H1299, A549, H23, and H1975 cells were seeded in triplicate at $1\times10^3$, $1\times10^3$, $1\times10^3$, $4\times10^3$, and $4\times10^3$ cells per well, respectively, in 96-well plates, using 200 µL of medium per well. Fresh drug was added every 24 hours by replacing medium with drug-containing medium. For all other assays, cells were seeded at $0.6$-$1.2\times10^5$ cells per well, in 6-well plates, using 4 mL of medium per well, with fresh drug added directly to the medium every 24 hours.

All six cell lines were treated with a dose range of AZA or DAC for 72 hours. Cell viability was assessed using the CyQuant assay (Life Technologies Corporation; Carlsbad, Calif.). Fluorescence was measured with a spectrophotometer (Molecular Devices; Sunnyvale, Calif.), and $EC_{50}$ values were calculated in Prism® version 5.01 (GraphPad Software, Inc.; La Jolla, Calif.), using results from three independent experiments.

The six data sets represent calculations of $EC_{50}$ values from raw data using Prism®. The standard deviation among the three independent experiments was determined at each drug concentration. For some of the cell lines, Prism® was not able to calculate the $EC_{50}$ for DAC. For those curves that an $EC_{50}$ was available, the SE (Std. Error) was acceptable (SE of the log $EC_{50}$ should be less than 0.5), meaning that the standard errors were not too large. The 95% Confidence Intervals for the $EC_{50}$ were considered as a measure of error. In this respect, 95% Confidence Intervals for the $EC_{50}$ of AZA were tighter than those of DAC. The AZA curves had sigmoidal shapes, while the DAC curves were not ideal. The AZA profiles indicated cytotoxic activities at high doses, whereas the DAC profiles indicated cytostatic activity at high doses.

TABLE 1

Effects of AZA and DAC on A549 Viability

|  | AZA | DAC |
|---|---|---|
| log(inhibitor) vs. normalized response -- Variable slope | | |
| Best-fit values | | |
| LogIC50 | 0.8033 | 1.556 |
| HillSlope | −1.108 | −0.4617 |
| IC50 | 6.358 | 35.94 |
| Std. Error | | |
| LogIC50 | 0.05164 | 0.1622 |
| HillSlope | 0.1431 | 0.07433 |
| 95% Confidence Intervals | | |
| LogIC50 | 0.6975 to 0.9090 | 1.223 to 1.888 |
| HillSlope | −1.401 to −0.8147 | −0.6139 to −0.3095 |
| IC50 | 4.984 to 8.110 | 16.72 to 77.24 |
| Goodness of Fit | | |
| Degrees of Freedom | 28 | 28 |
| $R^2$ | 0.8964 | 0.7420 |
| Absolute Sum of Squares | 2985 | 2279 |
| Sy.x | 10.33 | 9.022 |
| Number of points | | |
| Analyzed | 30 | 30 |

TABLE 2

Effects of AZA and DAC on H1975 Viability

|  | AZA | DAC |
|---|---|---|
| log(inhibitor) vs. normalized response -- Variable slope | | |
| Best-fit values | | |
| LogIC50 | 0.8897 | 2.452 |
| HillSlope | −0.6352 | −0.2958 |
| IC50 | 7.757 | 283.2 |
| Std. Error | | |
| LogIC50 | 0.04753 | 0.2765 |
| HillSlope | 0.04902 | 0.04165 |

TABLE 2-continued

Effects of AZA and DAC on H1975 Viability

|  | AZA | DAC |
|---|---|---|
| 95% Confidence Intervals |  |  |
| LogIC50 | 0.7923 to 0.9870 | 1.886 to 3.018 |
| HillSlope | −0.7356 to −0.5348 | −0.3811 to −0.2105 |
| IC50 | 6.199 to 9.706 | 76.85 to 1043 |
| Goodness of Fit |  |  |
| Degrees of Freedom | 28 | 28 |
| $R^2$ | 0.9324 | 0.7442 |
| Absolute Sum of Squares | 1056 | 852.6 |
| Sy.x | 6.140 | 5.518 |
| Number of points |  |  |
| Analyzed | 30 | 30 |

TABLE 3

Effects of AZA and DAC on H23 Viability

|  | AZA | DAC |
|---|---|---|
| log(inhibitor) vs. normalized response -- Variable slope |  |  |
| Best-fit values |  |  |
| LogIC50 | 1.005 | 1.268 |
| HillSlope | −1.054 | −0.3790 |
| IC50 | 10.12 | 18.53 |
| Std. Error |  |  |
| LogIC50 | 0.03840 | 0.1537 |
| HillSlope | 0.1024 | 0.05733 |
| 95% Confidence Intervals |  |  |
| LogIC50 | 0.9265 to 1.084 | 0.9531 to 1.583 |
| HillSlope | −1.264 to −0.8442 | −0.4964 to −0.2616 |
| IC50 | 8.443 to 12.13 | 8.976 to 38.25 |
| Goodness of Fit |  |  |
| Degrees of Freedom | 28 | 28 |
| $R^2$ | 0.9319 | 0.7371 |
| Absolute Sum of Squares | 1383 | 2601 |
| Sy.x | 7.027 | 9.638 |
| Number of points |  |  |
| Analyzed | 30 | 30 |

TABLE 4

Effects of AZA and DAC on H460 Viability

|  | AZA | DAC |
|---|---|---|
| log(inhibitor) vs. normalized response -- Variable slope |  |  |
| Best-fit values |  |  |
| LogIC50 | 0.2413 | 2.053 |
| HillSlope | −0.8940 | −0.3814 |
| IC50 | 1.743 | 113.1 |
| Std. Error |  |  |
| LogIC50 | 0.02470 | 0.2135 |
| HillSlope | 0.04327 | 0.05566 |
| 95% Confidence Intervals |  |  |
| LogIC50 | 0.1907 to 0.2919 | 1.616 to 2.491 |
| HillSlope | −0.9826 to −0.8054 | −0.4954 to −0.2674 |
| IC50 | 1.551 to 1.958 | 41.32 to 309.5 |
| Goodness of Fit |  |  |
| Degrees of Freedom | 28 | 28 |
| $R^2$ | 0.9818 | 0.7610 |

TABLE 4-continued

Effects of AZA and DAC on H460 Viability

|  | AZA | DAC |
|---|---|---|
| Absolute Sum of Squares | 573.1 | 1164 |
| Sy.x | 4.524 | 6.447 |
| Number of points |  |  |
| Analyzed | 30 | 30 |

TABLE 5

Effects of AZA and DAC on H1299 Viability

|  | AZA | DAC |
|---|---|---|
| log(inhibitor) vs. normalized response -- Variable slope |  |  |
| Best-fit values |  |  |
| LogIC50 | 0.7095 | 0.7153 |
| HillSlope | −1.138 | −0.4536 |
| IC50 | 5.123 | 5.192 |
| Std. Error |  |  |
| LogIC50 | 0.02413 | 0.09468 |
| HillSlope | 0.06863 | 0.05666 |
| 95% Confidence Intervals |  |  |
| LogIC50 | 0.6601 to 0.7590 | 0.5214 to 0.9092 |
| HillSlope | −1.279 to −0.9976 | −0.5696 to −0.3376 |
| IC50 | 4.572 to 5.741 | 3.322 to 8.114 |
| Goodness of Fit |  |  |
| Degrees of Freedom | 28 | 28 |
| $R^2$ | 0.9761 | 0.8154 |
| Absolute Sum of Squares | 687.4 | 2780 |
| Sy.x | 4.955 | 9.964 |
| Number of points |  |  |
| Analyzed | 30 | 30 |

TABLE 6

$EC_{50}$ of Effect of AZA and DAC on the Viability of NSCLC Cells

| NSCLC Cell Type | AZA $EC_{50}$ (μM) | DAC $EC_{50}$ (μM) |
|---|---|---|
| A549 | 6.4 | >25 |
| H1975 | 7.8 | >25 |
| H460 | 1.7 | >25 |
| H23 | 10.1 | 18.5 |
| H1299 | 5.1 | 5.2 |

6.2 Example 2

Cell cycle distribution studies were performed to differentiate the effects of two different azacytidine analogs, azacitidine (AZA) and decitabine (DAC), on various NSCLC cell types, and to study the mechanism of action of these two cytidine analogs. These studies examined the cell cycle distribution of NSCLC cells treated with AZA or DAC using NIM-DAPI analysis.

For cell cycle distribution, cells were stained with the NIM-DAPI reagent (Beckman Coulter, Inc.; Fullerton, Calif.). For measurement of early- and late-apoptotic cell populations, cells were stained with AnnexinV-FITC and 7-AAD reagents (Beckman Coulter, Inc.). Samples were processed according to manufacturer's instructions and analyzed on a Cell Lab Quanta MPL flow cytometer (Beckman Coulter, Inc.). For each study described below, cells were treated with AZA or DAC at a concentration of 0.3 μM, 1 μM, 3 μM, or 10 μM for a certain period of time. Data were also collected for untreated cells as control.

In one experiment, A549 cells were treated with AZA or DAC for 72 hours. NIM DAPI results were obtained. In A549 cells, AZA induced accumulation of cells in G2/M and Sub-G1 while DAC induced an increase of cells in G2/M (72-hour treatment).

In another experiment, A549 cells were treated with AZA or DAC for 48 hours. NIM DAPI results were obtained. In A549 cells, AZA induced accumulation of cells in G2/M and Sub-G1, while DAC induced an increase of cells in G2/M (48-hour treatment).

Figure 6:
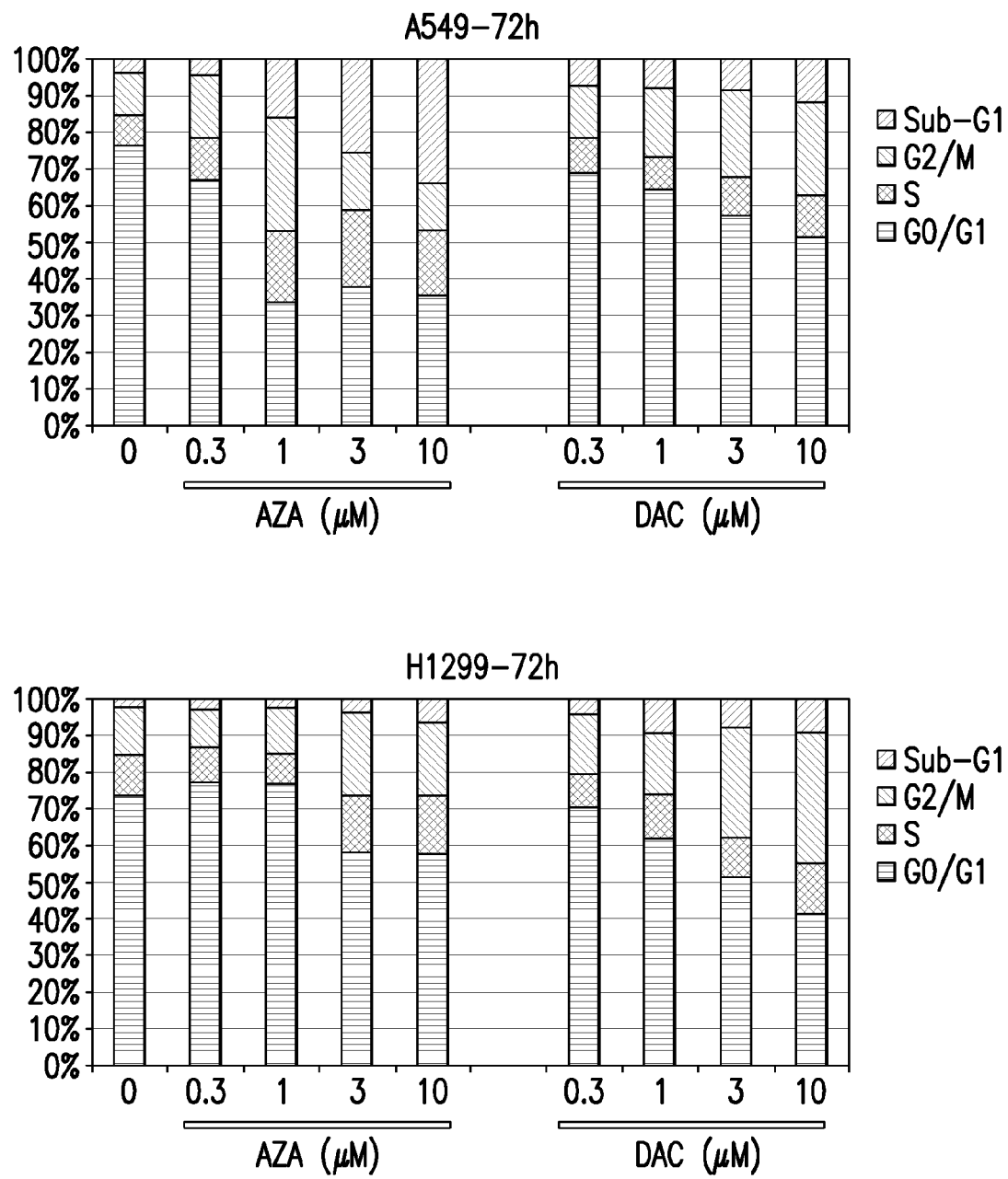
FIG. 6 represents NIM DAPI results from A549 cells treated with AZA or DAC for 72 h and from H1299 cells treated with AZA or DAC for 72 h.

In another experiment, A549 cells were treated with AZA or DAC for 72 hours. NIM DAPI results are shown in FIG. 6. In A549 cells, AZA induced accumulation of cells in G2/M and Sub-G1, while DAC induced an increase of cells in G2/M (72-hour treatment).

In another experiment, H1299 cells were treated with AZA or DAC for 72 hours. NIM DAPI results are shown in FIG. 6. In H1299 cells, AZA and DAC induced accumulation of cells in G2/M and Sub-G1 (72-hour treatment).

In another experiment, H1299 cells were treated with AZA or DAC for 48 hours. NIM DAPI results were obtained. In H1299 cells, DAC induced accumulation of cells in G2/M (48-hour treatment).

In another experiment, H1299 cells were treated with AZA or DAC for 72 hours. NIM DAPI results were obtained. In H1299 cells, AZA and DAC induced accumulation of cells in Sub-G1 while DAC also caused an increase of cells in G2/M (72-hour treatment).

In another experiment, H1975 cells were treated with AZA or DAC for 72 hours. NIM DAPI results were obtained. In H1975 cells, AZA treatment led to decrease of cells in G0/G1 and accumulation of cells in G2/M and Sub-G1. DAC treatment led to slight increases in G2/M and Sub-G1 (72-hour treatment).

In another experiment, H460 cells were treated with AZA or DAC for 30 hours. NIM DAPI results were obtained. In H460 cells, AZA and DAC induced accumulation of cells in Sub-G1 (30-hour treatment).

In another experiment, 11460 Cells were treated with AZA or DAC for 60 hours. NIM DAPI results were obtained. In H460 cells, AZA treatment led to decrease of cells in G0/G1 with a concomitant increase of cells in Sub-G1. DAC treatment led to slight increase in Sub-G1 (60-hour treatment).

6.3 Example 3

Apoptosis studies were performed to differentiate the effects of two different azacytidine analogs, azacitidine (AZA) and decitabine (DAC), on various NSCLC cell types, and to study the mechanism of action of these two cytidine analogs. These studies examined the apoptosis effect of NSCLC cells treated with AZA or DAC using AnnexinV-FITC/7-AAD.

For cell cycle distribution, cells were stained with the NIM-DAPI reagent (Beckman Coulter, Inc.; Fullerton, Calif.). For measurement of early- and late-apoptotic cell populations, cells were stained with AnnexinV-FITC and 7-AAD reagents (Beckman Coulter, Inc.). Samples were processed according to manufacturer's instructions and analyzed on a Cell Lab Quanta MPL flow cytometer (Beckman Coulter, Inc.). For each study described below, cells were treated with AZA or DAC at a concentration of 0.3 μM, 1 μM, 3 μM or 10 μM for a certain period of time. Data were also collected for untreated cells as control.

In one experiment, H460 cells were treated with AZA or DAC for 30 hours. AnnexinV/7-AAD results were obtained. In H460 cells, AZA treatment led to dramatic increase in early-apoptotic (AnnexinV$^+$ 7-AAD$^-$) and late-apoptotic (AnnexinV$^+$ 7-AAD$^+$) cells, while DAC treatment led to very slight increase in these cell populations (30-hour treatment).

Figure 8:
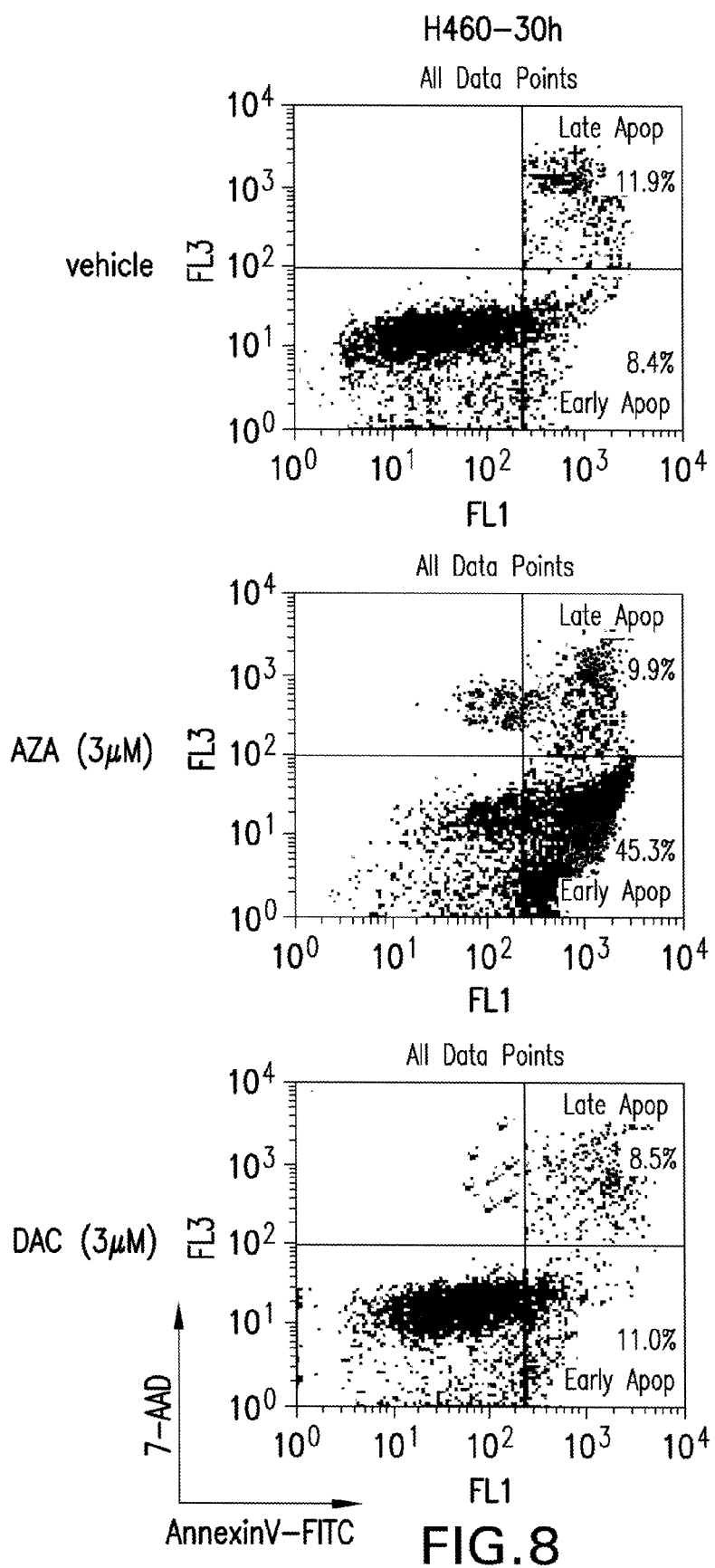
FIG. 8 represents AnnexinV/7-AAD results from H460 cells treated with AZA or DAC for 30 h.

In another experiment, H460 cells were treated with AZA or DAC for 30 hours. AnnexinV/7-AAD results are shown in FIG. 8. In H460 cells, AZA treatment led to dramatic increase in early-apoptotic (AnnexinV$^+$ 7-AAD$^-$) cells, while DAC treatment led to very slight increase in this cell population (30-hour treatment).

In another experiment, H460 cells were treated with AZA or DAC for 48 hours. AnnexinV/7-AAD results were obtained. In H460 cells, AZA treatment led to dramatic increase in early-apoptotic (AnnexinV$^+$ 7-AAD$^-$) cells, while DAC treatment led to some increase in this cell population (48-hour treatment).

Figure 7:
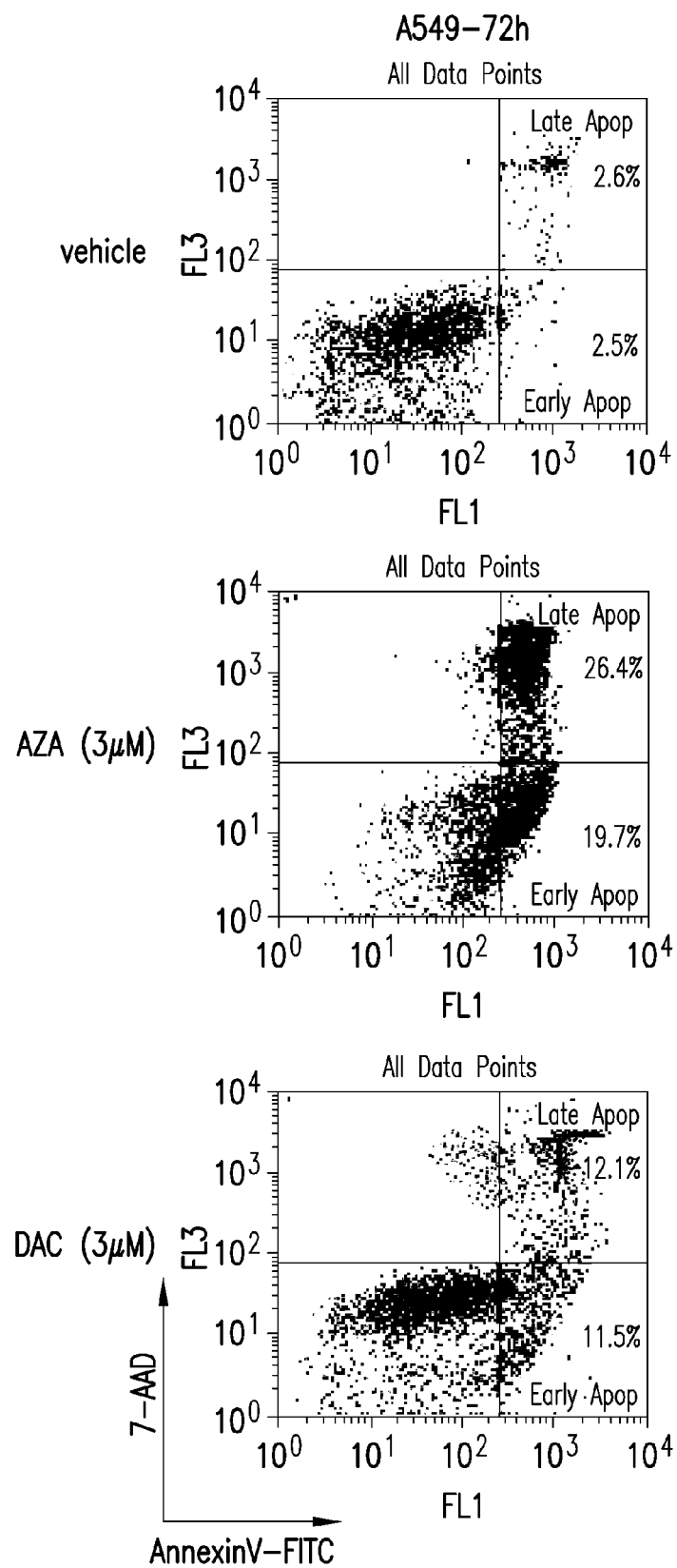
FIG. 7 represents AnnexinV/7-AAD results from A549 cells treated with AZA or DAC for 72 h.

In another experiment, A549 cells were treated with AZA or DAC for 72 hours. AnnexinV/7-AAD results are shown in FIG. 7. In A549 cells, AZA treatment led to dramatic increase in early-apoptotic (AnnexinV$^+$ 7-AAD$^-$) and late-apoptotic (AnnexinV$^+$ 7-AAD$^+$) cells, while DAC treatment led to very slight increase in these cell populations (72-hour treatment).

In another experiment, A549 cells were treated with AZA or DAC for 48 hours. AnnexinV/7-AAD results were obtained. In A549 cells, AZA treatment led to dramatic increase in early-apoptotic (AnnexinV$^+$ 7-AAD$^-$) and late-apoptotic (AnnexinV$^+$ 7-AAD$^+$) cells, while DAC treatment led to very slight increase in these cell populations (48-hour treatment).

In another experiment, A549 cells were treated with AZA or DAC for 72 hours. AnnexinV/7-AAD results were obtained. In A549 cells, AZA treatment led to dramatic increase in early-apoptotic (AnnexinV$^+$ 7-AAD$^-$) and late-apoptotic (AnnexinV$^+$ 7-AAD$^-$) cells, while DAC treatment led to slight increase in early-apoptotic (AnnexinV$^+$7-AAD$^-$) cells only (72-hour treatment).

In another experiment, H1299 cells were treated with AZA or DAC for 72 hours. AnnexinV/7-AAD results were obtained. In H1299 cells, AZA treatment led to dramatic increase in early-apoptotic (AnnexinV$^+$ 7-AAD$^-$) and late-apoptotic (AnnexinV$^+$ 7-AAD$^-$) cells, while DAC treatment led to very slight increase in these cell populations (72-hour treatment).

In another experiment, H1299 cells were treated with AZA or DAC for 48 hours. AnnexinV/7-AAD results were obtained. In H1299 cells, AZA treatment led to dramatic increase in early-apoptotic (AnnexinV$^+$ 7-AAD$^-$) and late-apoptotic (AnnexinV$^+$ 7-AAD$^+$) cells, while DAC treatment led to very slight increase in these cell populations (48-hour treatment).

Figure 9:
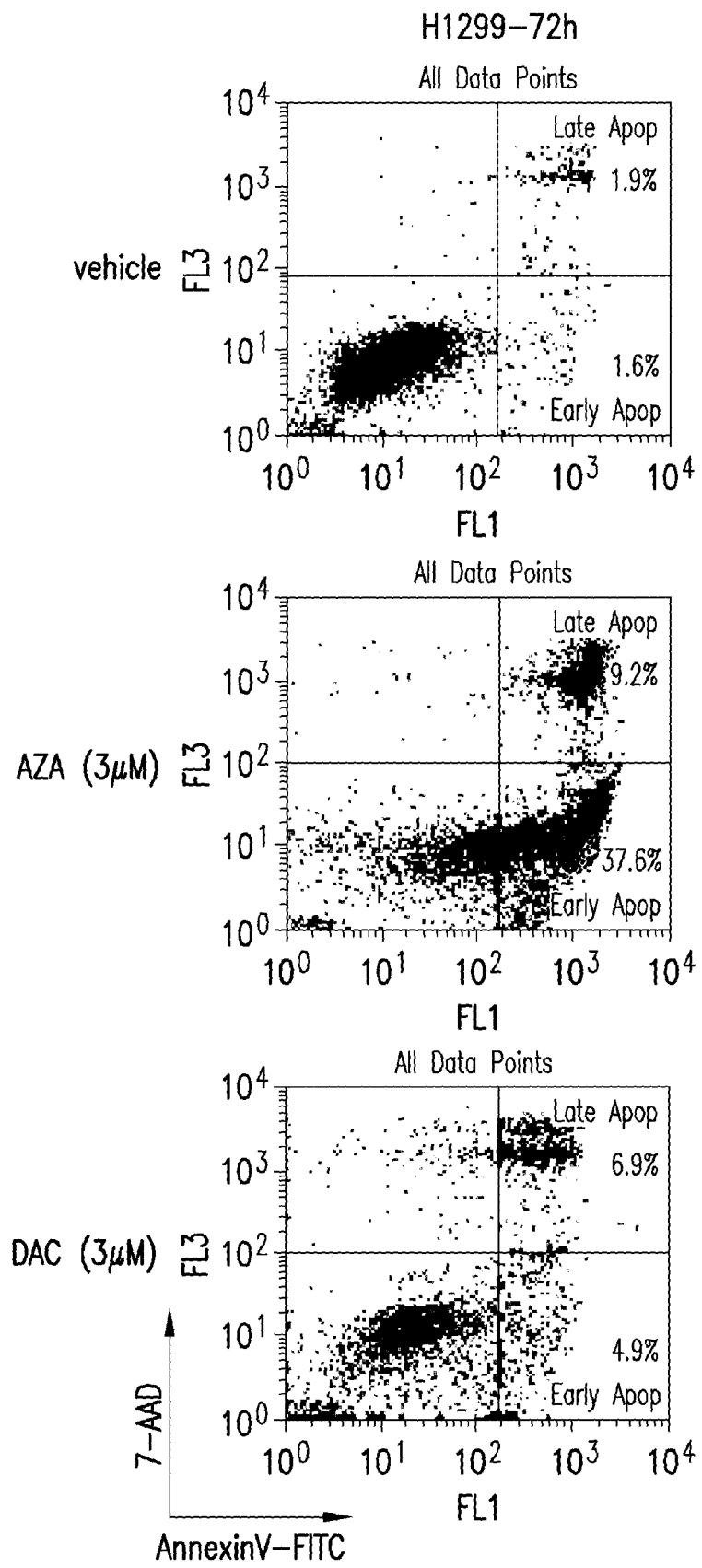
FIG. 9 represents AnnexinV/7-AAD results from H1299 cells treated with AZA or DAC for 72 h.

In another experiment, H1299 cells were treated with AZA or DAC for 72 hours. AnnexinV/7-AAD results are shown in FIG. 9. In H1299 cells, AZA treatment led to dramatic increase in early-apoptotic (AnnexinV$^+$ 7-AAD$^-$) and late-apoptotic (AnnexinV$^+$ 7-AAD$^+$) cells, while DAC treatment led to very slight increase in these cell populations (72-hour treatment).

These studies indicated the following: (1) NIM-DAPI results for A549 cells indicated that AZA induced accumulation of cells in G2/M and Sub-G1 while DAC induced an increase of cells in G2/M; (2) NIM-DAPI results for H1299 cells suggested that AZA and DAC induced accumulation of cells in Sub-G1 while DAC also caused an increase of cells in G2/M; (3) NIM-DAPI results for H460 cells suggested that both AZA and DAC induced accumulation of cells in Sub-G1;

(4) AnnexinV-FITC/7-AAD results indicated that AZA treatment led to dramatic increase in early-apoptotic (AnnexinV+ 7-AAD−) and late-apoptotic (AnnexinV+7-AAD+) cells, while DAC treatment led to very slight increase in these cell populations.

6.4 Example 4

Methylation assays were performed to study the effects of two different azacytidine analogs, azacitidine (AZA) and decitabine (DAC), on various NSCLC cell types, and to study the mechanism of action of these two cytidine analogs. These studies examined the methylation effects on NSCLC cells treated with AZA or DAC using the LINE-1 Methylation Assay.

Genomic DNA was purified from cells using the DNeasy Blood and Tissue Kit (Qiagen; Valencia, Calif.), according to the manufacturer's instructions. DNA yield was quantitated with a NanoDrop 8000 spectrophotometer (Thermo Fisher Scientific, Inc.). DNAs (1 μg/sample) were submitted to EpigenDx (Worcester, Mass.) for bisulfite conversion and pyrosequencing of LINE-1 elements. Briefly, 1 μg of DNA was bisulfite-treated using the Zymo DNA Methylation Kit (Zymo Research; Orange, Calif.) and eluted in 10 μL volume. DNA eluate (1 μL) was used for PCR with biotinylated primers to the LINE-1 locus, converting the PCR product to single-stranded DNA templates. PCR products (each 10 μL) were sequenced by Pyrosequencing PSQ96 HS System (Biotage AB), following the manufacturer's instructions (Biotage; Kungsgatan, Sweden). The methylation status of each locus was analyzed individually as a T/C SNP using QCpG software (Biotage). Percent LINE-1 methylation represents the average percent methylation of four CpG sites in duplicate samples.

Cells of the A549 cell type were treated with AZA or DAC for 48 hours or 72 hours. Cells of the H1299 cell type were treated with AZA or DAC for 48 hours or 72 hours. The studies indicated that both AZA and DAC induced DNA hypomethylation in A549 cells and H1299 cells, as estimated with the LINE-1 Methylation Assay. The extent of hypomethylation appeared to be similar for both AZA and DAC at the 48 hour and 72 hour time points.

These studies indicated that both AZA and DAC induced DNA hypomethylation in A549 and H1299 cells.

6.5 Example 5

DNA damage and apoptosis studies were performed to differentiate the effects of two different azacytidine analogs, azacitidine (AZA) and decitabine (DAC), on various NSCLC cell types, and to study the mechanism of action of these two cytidine analogs. These studies examined the DNA damage of NSCLC cells treated with AZA or DAC at a concentration of 0.3 μM, 1 μM, 3 μM, or 10 μM, for 24 hours, 48 hours, 72 hours, or 144 hours (FIGS. 10-12 and 14) using an assay for Histone H2AX (Ser139) phosphorylation. These studies also examined apoptosis using an assay for PARP cleavage. Cells studied included H460, A549, and H1299 cells.

For western analyses of protein levels, cells were washed with PBS and lysed with RIPA buffer (Cell Signaling Technology, Inc.; Danvers, Mass.) containing 350 mM NaCl and 0.1% SDS. Cell lysates were sonicated with two 5-second bursts under low amplitude (20%) using the Digital Sonic Dismembrator (Thermo Fisher Scientific, Inc.; Waltham, Mass.). Proteins were separated on 4-12% Bis-Tris NuPAGE gels (Life Technologies Corporation) and transferred to nitrocellulose membranes. DNMT1, phos-Histone-H2AX (Ser139), total Histone-H2AX, cleaved-PARP, p21, p53, and alpha-tubulin were detected using the Li-Cor Odyssey imaging system (Li-Cor Biotechnology; Lincoln, Nebr.), following incubation with the appropriate primary and secondary antibodies. The phos-Histone-H2AX(Ser139), cleaved-PARP, and p21 antibodies were from Cell Signaling Technology, Inc. The p53 and total Histone-H2AX (C-20) antibodies were from Santa Cruz Biotechnology, Inc. (Santa Cruz, Calif.). The alpha-tubulin and DNMT1 antibodies were purchased from EMD Chemicals, Inc. (Gibbstown, N.J.) and Abcam, Inc. (Cambridge, Mass.), respectively. The goat anti-Rabbit IRDye 680, goat anti-Mouse IRDye 800CW, and donkey anti-Goat IRDye 800CW secondary antibodies were from Li-Cor Biotechnology.

Figure 10:
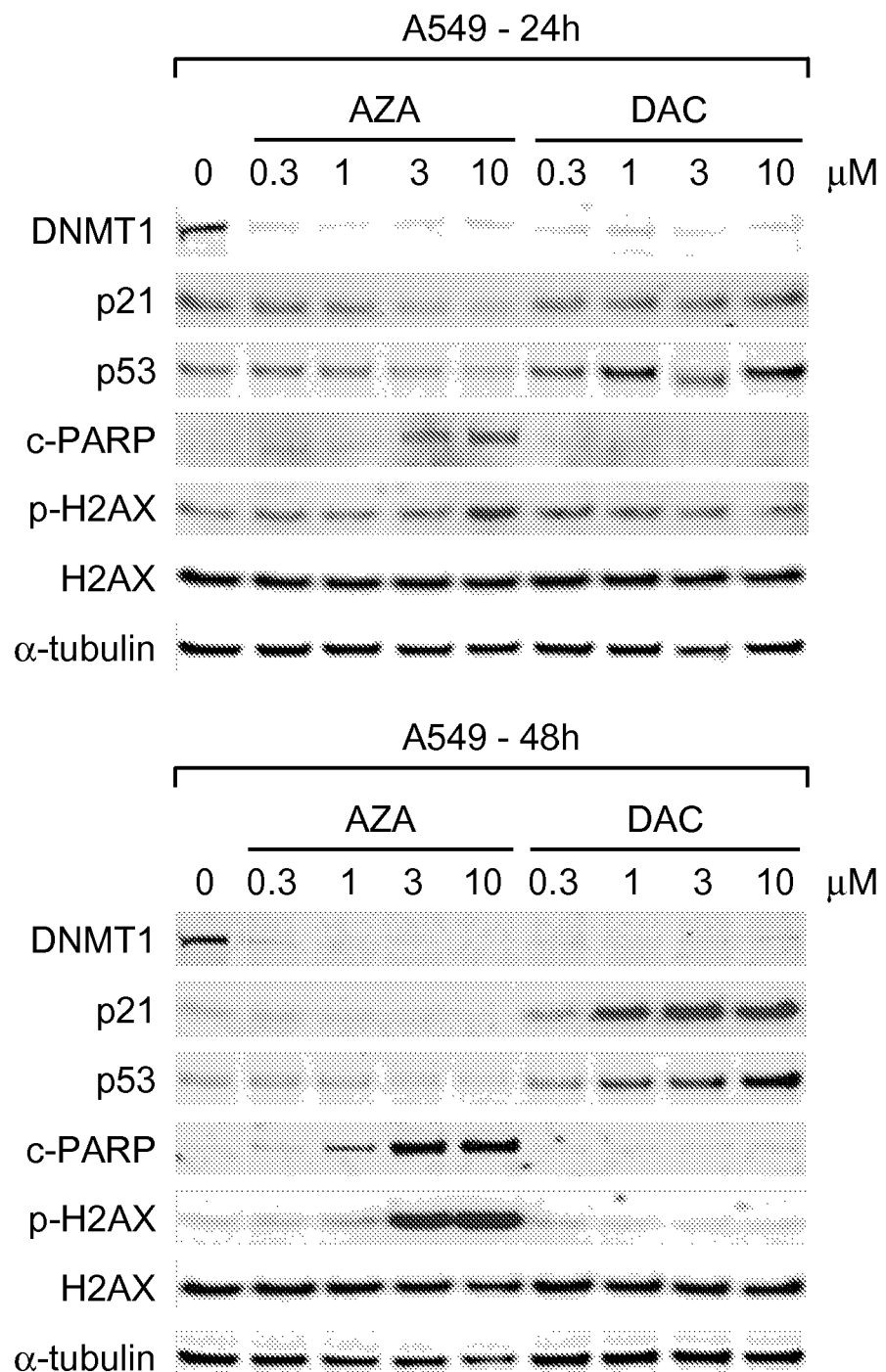
FIG. 10 represents results of cell-based assays, including DNMT1 depletion, p21, p53, Histone H2AX phosphorylation (a marker of DNA damage) and PARP cleavage (a marker of apoptosis) in A549 cells treated with AZA or DAC at particular concentrations for 24 h and 48 h.

A549 Cells: AZA, but not DAC, induced Histone H2AX phosphorylation (marker of DNA damage) and PARP cleavage (marker of apoptosis) in A549 cells. AZA appeared to be more potent at inducing these markers through time. Although DAC did not have any effect on these markers, DAC was not inactive since it was able to cause DNMT1 depletion as well as induce p21 and p53 expression. Results are shown in FIG. 10.

Figure 11:
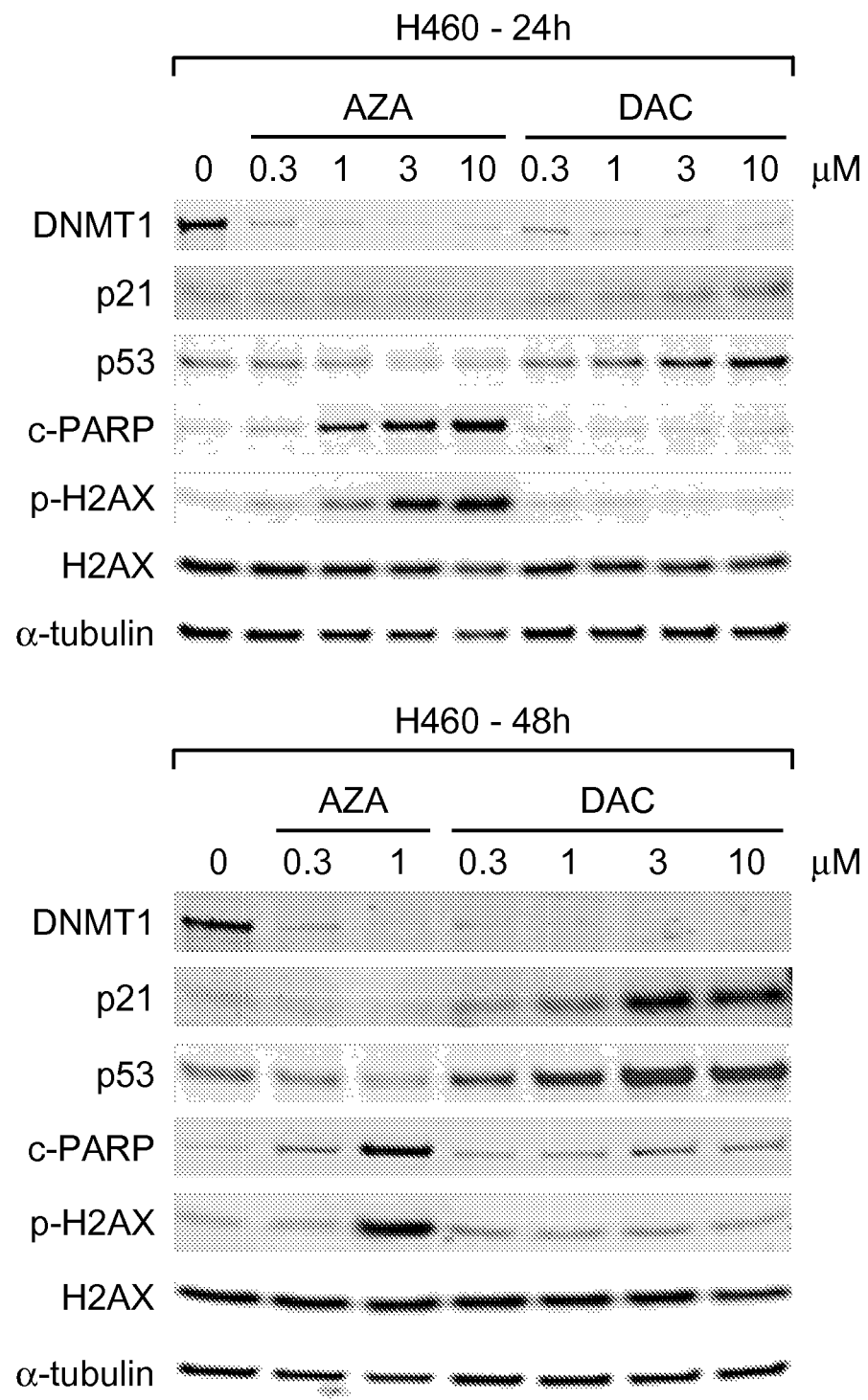
FIG. 11 represents results of cell-based assays, including DNMT1 depletion, p21, p53, Histone H2AX phosphorylation (a marker of DNA damage) and PARP cleavage (a marker of apoptosis) in H460 cells treated with AZA or DAC at particular concentrations for 24 h and 48 h.

H460 Cells: AZA, but not DAC, induced Histone H2AX phosphorylation and PARP cleavage in H460 cells. AZA affected these markers at concentrations above 1 μM ($EC_{50}$ of AZA in these cells was 1.237 μM). Although DAC did not have any effect on these markers, DAC was not inactive since it was able to cause DNMT1 depletion as well as induce p21 and p53 expression (in dose-dependent manner). Results are shown in FIG. 11.

Figure 12:
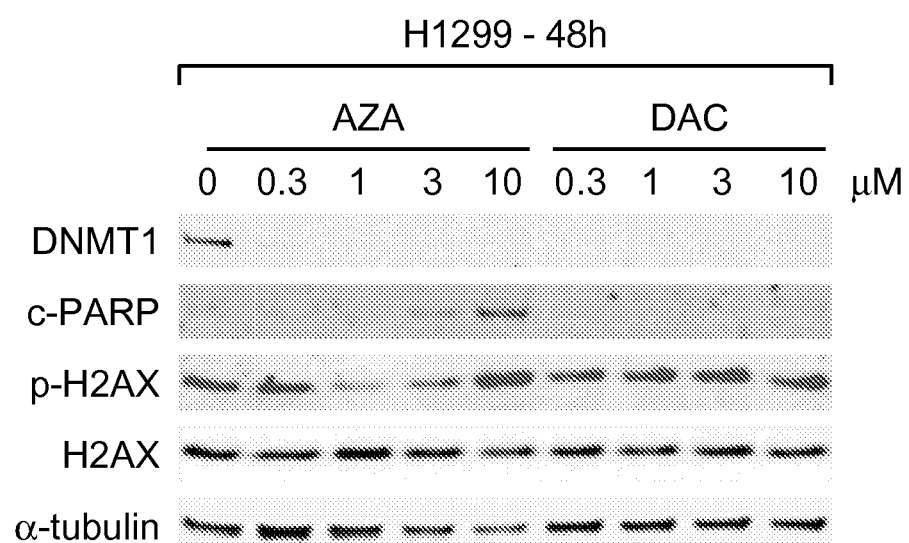
FIG. 12 represents results of cell-based assays, including DNMT1 depletion, Histone H2AX phosphorylation (a marker of DNA damage) and PARP cleavage (a marker of apoptosis) in H1299 cells treated with AZA or DAC at particular concentrations for 48 h.

H1299 Cells: AZA, but not DAC, induced Histone H2AX phosphorylation and PARP cleavage in H1299 cells after up to 3 days of treatment. AZA affected these markers at concentrations above 3 μM ($EC_{50}$ of AZA in these cells was 5.1 μM). Although DAC did not have any effect on these markers, DAC did not appear to be inactive since it was able to cause DNMT1 depletion in these cells. The study did not probe for p53, because p53 is null in H1299 cells; correspondingly, no regulation of p21 was observed. Results are shown in FIG. 12.

These studies indicated the following: (1) AZA, but not DAC, induced Histone H2AX phosphorylation in H460, A549, and H1299 cells up to the 72 hour time point (DAC induced Histone H2AX phosphorylation at 6 days in H1299 cells); (2) AZA, but not DAC, induced PARP cleavage in H1460, A549, and H1299 cells; and (3) AZA induces DNA damage and cell death markers at lower concentrations than DAC.

6.6 Example 6

Gene expression in NSCLC cells was analyzed to differentiate the effects of two different azacytidine analogs, azacitidine (AZA) and decitabine (DAC), on various NSCLC cell types, and to study the mechanism of action of these two cytidine analogs. These studies examined the effects on gene expression in NSCLC cells treated with AZA or DAC.

Cells were lysed using the TRIzol reagent (Life Technologies Corporation) and total RNA was isolated using miRNeasy (Qiagen). Double-stranded cDNA and biotin-labeled cRNA were synthesized using 100 ng of total RNA using Ambion's MessageAmp Premier RNA Amplification Kit (ABI; Foster City, Calif.). Biotin-labeled cRNA, at 10 μg, was fragmented and hybridized to each human U133A 2.0 genechip (Affymetrix; Santa Clara, Calif.). The GC-RMA algorithm was used for normalization and all analyses were done using GeneSpring 7.3 (Agilent; Santa Clara, Calif.). Averaged signals from biological duplicate samples were used to determine fold change (Treated vs. Untreated), with an absolute fold change of ≧1.7 defining regulated genes. NextBio was used to identify regulated Gene Ontology biogroups from lists of regulated genes. The top 15 biogroups are those with the lowest p-values calculated within NextBio.

A549 and H1299 cells were treated with a dose range (0.3-3 µM) of AZA or DAC for 48 hours, and effects on gene expression were assessed by microarray analysis. The total number of genes regulated by AZA or DAC, and the overlap of genes regulated by each drug, are presented in Table 7. At the lower drug concentration (0.3 µM), AZA and DAC modulated few genes, with DAC modulating 4- to 20-fold more genes than AZA. At the higher drug concentrations (1 and 3 µM), many more genes were modulated, with AZA modulating 2- to 5-fold more genes than DAC. The number of genes modulated in common between the two drugs was low.

Figure 13:
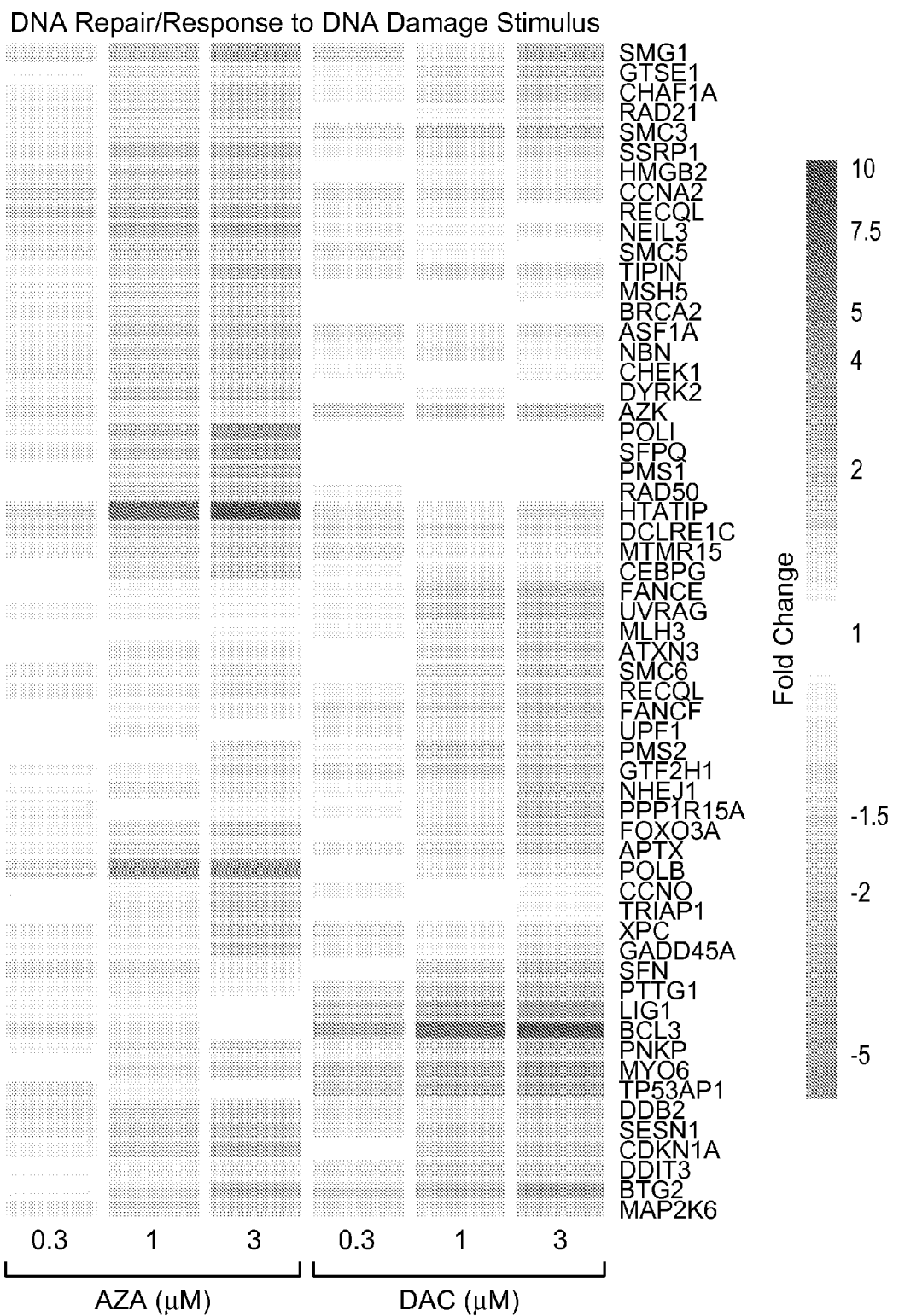
FIG. 13 represents the gene expression profile of A549 cells after 48 hours of treatment with AZA or DAC at particular concentrations, showing a general upregulation of genes in the "Response to DNA Damage Stimulus/DNA Repair" biogroup in AZA-treated cells; DAC treatment caused a general downregulation of genes within this group.

Functional groupings of the modulated genes were determined using Gene Ontology classifications in Nextbio (http://www.nextbio.com/). AZA and DAC regulated very different biogroups in A549 and H1299 cells and the top 15 biogroups regulated by each drug (at 3 µM) are shown in Tables 8-9. AZA treatment of A549 cells caused a general upregulation of genes within the "Response to DNA Damage Stimulus/DNA Repair" biogroup (FIG. 13). These results were consistent with the induction of the dsDNA damage marker (Histone-H2AX(Ser139) phosphorylation) by AZA in these cells (Example 5). On the contrary, DAC treatment of A549 caused a general downregulation of genes within this biogroup. Collectively, these results indicated that AZA and DAC regulate different molecular pathways inside the cell and reflect the cell biology observed in other cellular assays.

TABLE 7

Number of Genes Regulated by AZA and/or DAC

| | | Upregulated Genes | | | Downregulated Genes | | |
|---|---|---|---|---|---|---|---|
| Cell Line | [Drug] (µM) | AZA-Specific Genes | Genes in Common | DAC-Specific Genes | AZA-Specific Genes | Genes in Common | DAC-Specific Genes |
| A549 | 0.3 | 16 | 17 | 139 | 14 | 11 | 55 |
| A549 | 1.0 | 279 | 45 | 261 | 273 | 30 | 111 |
| A549 | 3.0 | 636 | 66 | 413 | 560 | 55 | 239 |
| H1299 | 0.3 | 10 | 55 | 214 | 33 | 45 | 121 |
| H1299 | 1.0 | 435 | 135 | 238 | 393 | 107 | 170 |
| H1299 | 3.0 | 1368 | 173 | 303 | 991 | 153 | 257 |

TABLE 8

Top 15 Biogroups Regulated by AZA or DAC in A549 Cells
A549 - 48 h

| AZA (3 µM) | DAC (3 µM) |
|---|---|
| proteinaceous extracellular matrix ↓* | mitosis ↓* |
| extracellular matrix ↓ | cell cycle ↓ |
| transcription ↑ | cell division ↓ |
| extracellular matrix structural constituent ↓ | transferase activity, transferring sulfur-containing groups ↑ |
| glycosaminoglycan binding ↓ | meiosis ↓ |
| polysaccharide binding ↓ | meiotic cell cycle ↓ |
| pattern binding ↓ | response to DNA damage stimulus ↓ |
| lipid biosynthetic process ↓ | male gamete generation ↑ |
| fibrillar collagen ↓ | response to endogenous stimulus ↓ |
| calcium ion binding ↓ | chromosome segregation ↓ |
| fibrinogen complex ↓ | aromatic compound metabolic process ↑ |
| humoral immune response ↓ | phenol metabolic process ↑ |

TABLE 8-continued

Top 15 Biogroups Regulated by AZA or DAC in A549 Cells
A549 - 48 h

| AZA (3 µM) | DAC (3 µM) |
|---|---|
| protein binding, bridging ↓ | structural constituent of cytoskeleton ↑ |
| collagen ↓ | sister chromatid cohesion ↓ |
| response to wounding ↓ | cellular lipid catabolic process ↑ |

TABLE 9

Top 15 Biogroups Regulated by AZA or DAC in H1299 Cells
H1299 - 48 h

| AZA (3 µM) | DAC (3 µM) |
|---|---|
| transcription ↑* | cofactor binding ↓* |
| cell cycle ↓ | lipid metabolic process ↓ |
| mitosis ↓ | cell differentiation ↑ |
| cell division ↓ | coenzyme binding ↓ |
| cytoskeleton ↓ | transcription ↑ |
| microtubule ↓ | inner ear development ↑ |
| spindle ↓ | cell fate determination ↑ |
| mitochondrion ↓ | fatty acid metabolic process ↓ |
| sterol metabolic process ↓ | collagen binding ↑ |
| chromosome ↓ | oxidoreductase activity, acting on CH—OH group of donors, NAD/NADP as acceptor ↓ |
| alcohol metabolic process ↓ | enzyme inhibitor activity ↑ |
| ligase activity ↑ | nucleosome ↑ |
| lipid biosynthetic process ↓ | aldehyde metabolic process ↓ |
| steroid biosynthetic process ↓ | sensory organ development ↑ |
| mitotic sister chromatid segregation ↓ | oxidoreductase activity, acting on CH—OH group of donors ↓ |

6.7 Example 7

As shown in Example 5, 48-hour treatment with AZA, but not DAC, induced double-strand DNA damage (Histone-H2AX phosphorylation) in A549, H460, and H1299 cells (FIGS. 10-12). To better define the DNA damage response of NSCLC cell lines treated with AZA and DAC, NSCLC cell lines were treated with the AZA or DAC for an extended period of time.

Figure 14:
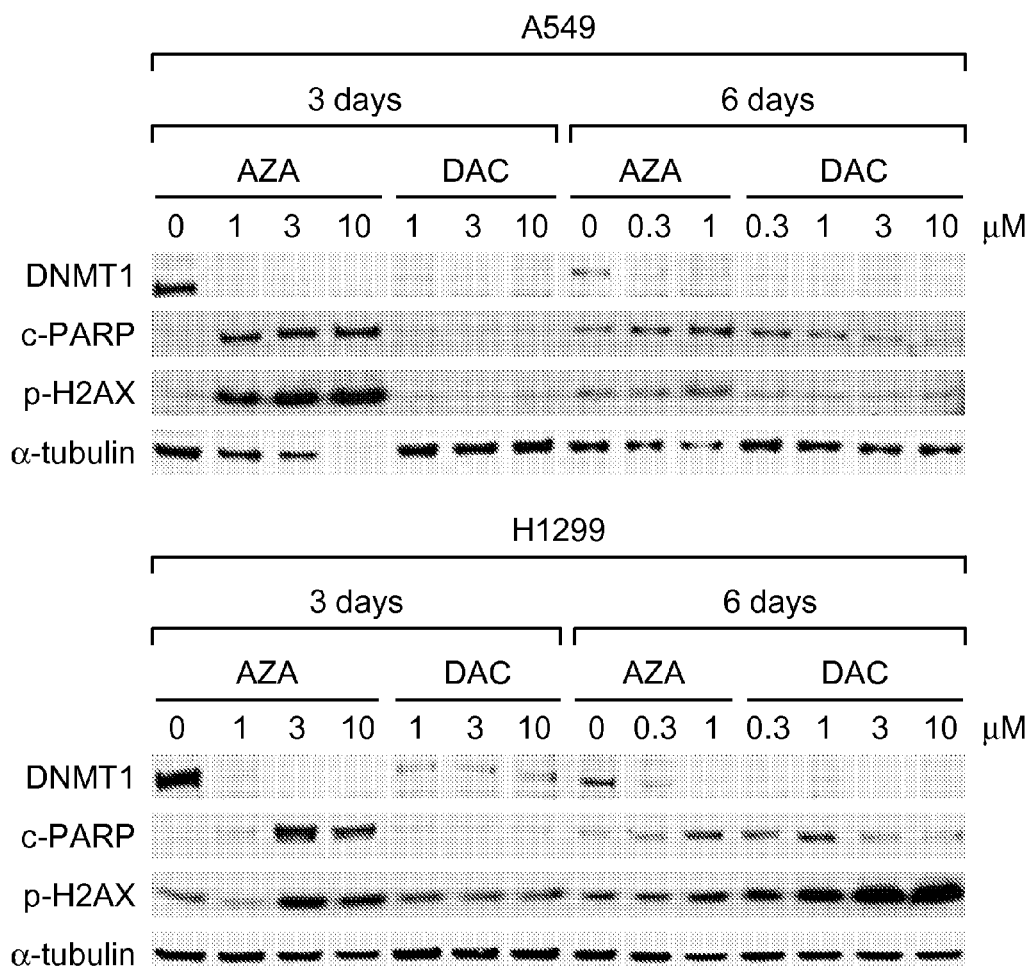
FIG. 14 represents results of cell-based assays, including DNMT1 depletion, Histone H2AX phosphorylation (a marker of DNA damage) and PARP cleavage (a marker of apoptosis) in A549 and H1299 cells treated with AZA or DAC at particular concentrations for 3 days or 6 days.

A549 and H1299 cells were treated with a dose-range of AZA or DAC for 6 days and lysates were collected on Days 3 and 6. At the 3-day time point in both cell lines, the results were similar to those at the 24- and 48-hour time points; AZA, but not DAC, induced Histone-H2AX phosphorylation and PARP cleavage (FIG. 14). In A549 cells, even after 6 days of treatment with DAC, there was a lack of induction of Histone-H2AX phosphorylation and PARP cleavage. In H1299 cells, although DAC did not induce Histone-H2AX phosphorylation after 3 days of treatment, DAC induced strong Histone-H2AX phosphorylation after 6 days of treatment. Thus, in H1299 cells, AZA induced double-strand DNA damage at an early time point, while DAC induced double-strand DNA damage at a later time point. Although there was a robust induction of Histone-H2AX phosphorylation in H1299 cells after 6 days of DAC treatment, DAC failed to induce significant PARP cleavage in these cells at this time point.

6.8 Example 8

Figure 15:
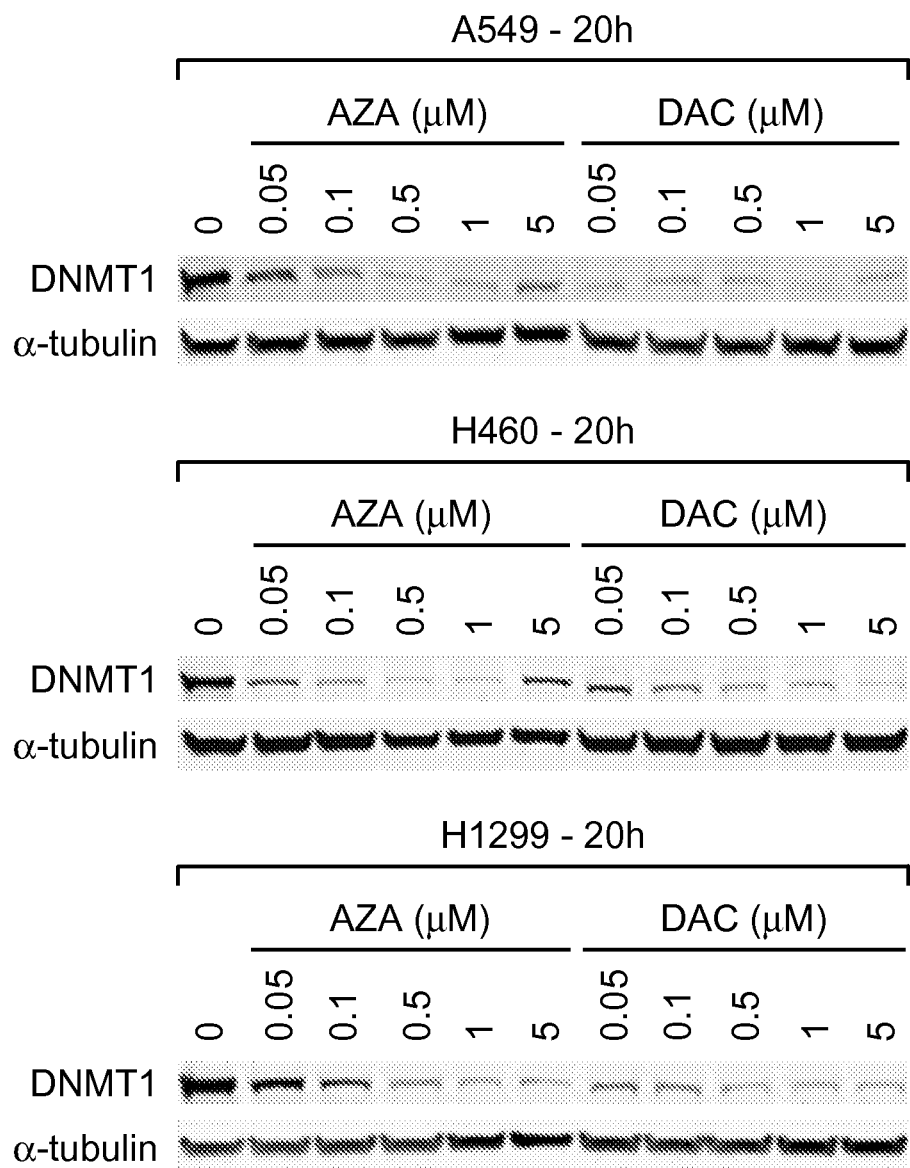
FIG. 15 represents results of cell-based assays on DNMT1 depletion in A549, H460, and H1299 cells treated with AZA or DAC at particular concentrations for 20 h.
Figure 17:
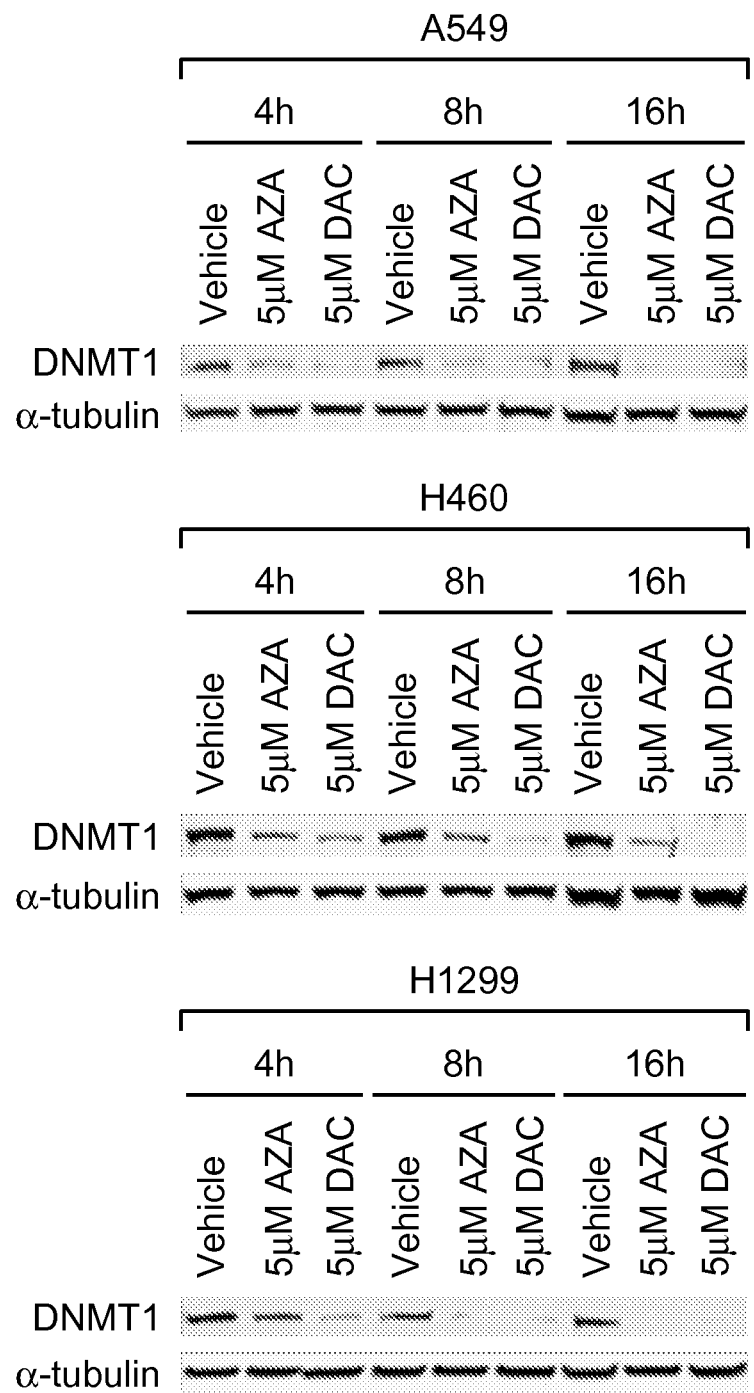
FIG. 17 represents results of cell-based assays on DNMT1 depletion in A549, H460, and H1299 cells treated with AZA or DAC at 5 µM for 4 h, 8 h, and 16 h.

To determine whether the differential sensitivity of NSCLC cell lines to AZA as compared to DAC in cell viability assays reflected a difference in the incorporation of each drug into DNA, DNMT1 protein depletion and DNA hypomethylation were evaluated as indirect measures of drug incorporation into DNA. A549, H460, and H1299 NSCLC cell lines were treated with a dose range of AZA or DAC for 20 hours. DNMT1 protein levels were significantly reduced by both AZA and DAC (FIG. 15). A dose-dependent decrease in DNMT1 levels was observed in all cases, except for A549 cells treated with DAC, where maximal reduction was observed at the lowest concentration (0.05 µM). In A549 and H1299 cells, DAC was more potent than AZA in reducing DNMT1 levels. In H460 cells, AZA and DAC were equipotent in reducing DNMT1 levels (FIG. 15). Reduced DNMT1 levels were detected in these cell lines as early as 4 hours after drug treatment (FIG. 17). AZA and DAC also caused time- and dose-dependent depletion of DNMT1 in the H23 cell line.

Figure 16:
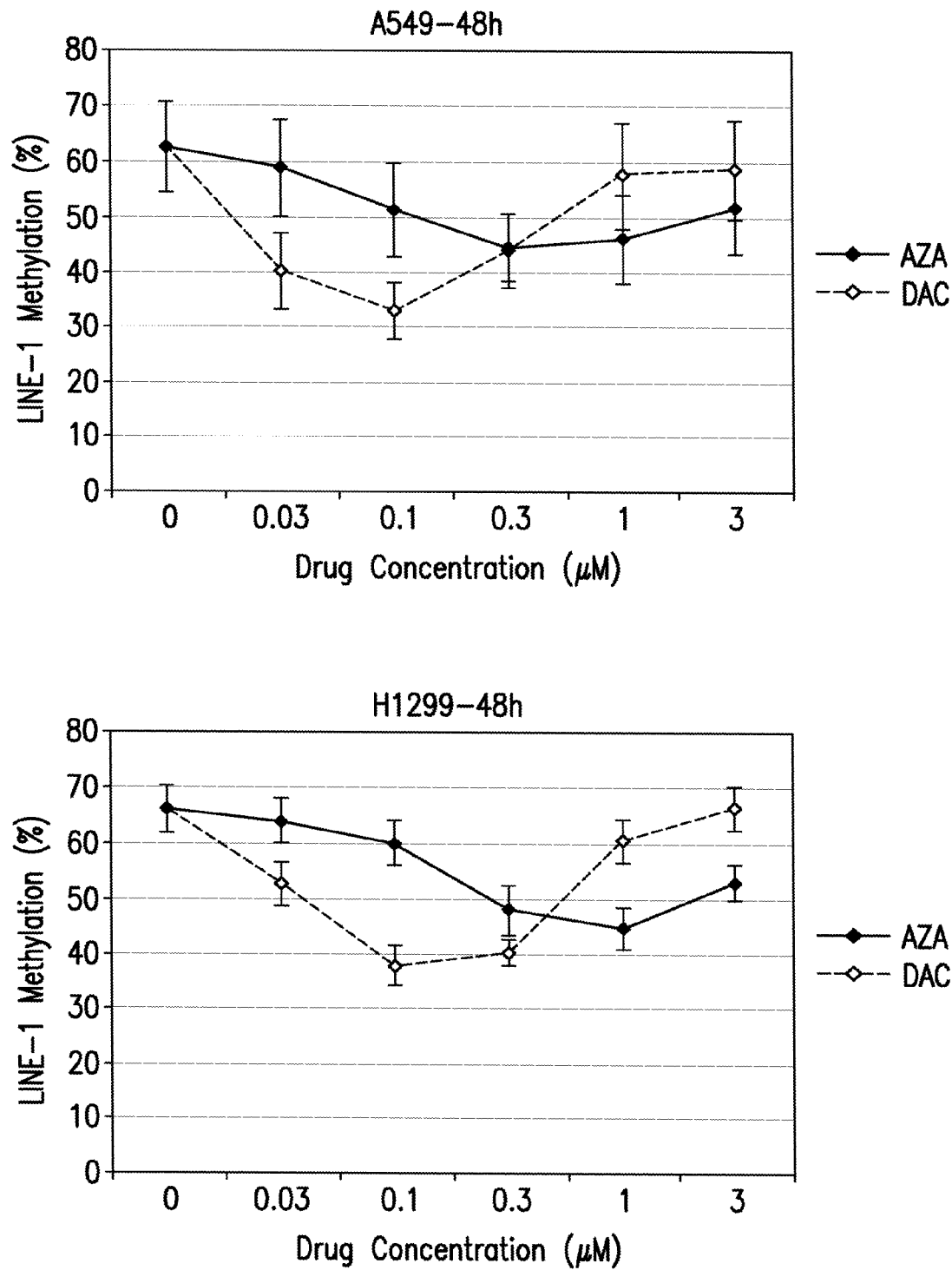
FIG. 16 represents results of cell-based assays on LINE-1 DNA methylation in A549 and H1299 cells treated with AZA or DAC at particular concentrations for 48 h.
Figure 18:
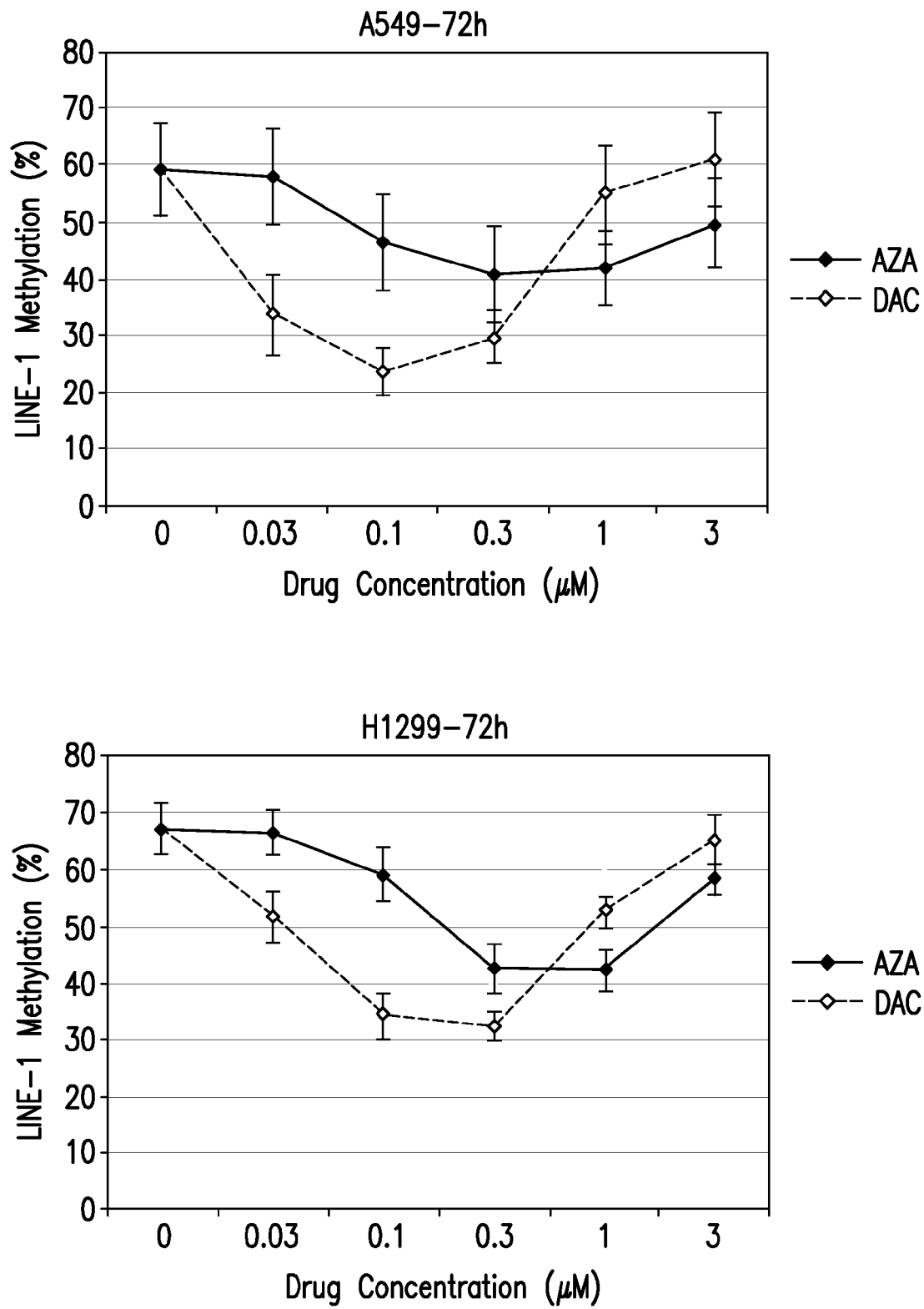
FIG. 18 represents results of cell-based assays on LINE-1 DNA methylation in A549 and H1299 cells treated with AZA or DAC at particular concentrations for 72 h.

To determine whether AZA and DAC caused DNA hypomethylation, the methylation status of LINE-1 elements in A549 and H1299 cells treated with a dose range of AZA or DAC for 48 hours (FIG. 16) or 72 hours (FIG. 18) were examined. AZA and DAC both caused a decrease in LINE-1 methylation. DAC was 3- to 10-fold more potent than AZA. Peak hypomethylation was observed at AZA concentrations of 0.3-1 µM and a DAC concentration of 0.1 µM. At the highest drug concentration tested (3 µM), LINE-1 methylation was less affected, possibly due to reduced drug incorporation as a result of inhibited cell proliferation.

These results suggest that AZA and DAC are incorporated into DNA, inducing DNMT1 depletion and DNA hypomethylation. These DNA-mediated events occurred in DAC-treated cells that were relatively unaffected by DAC in cell viability assays. Therefore, the lack of sensitivity to DAC in cell viability assays cannot be attributed to a lack of drug activation and DNA incorporation. These findings suggest that mechanisms in addition to, or other than, DNA hypomethylation are important for AZA-mediated reduction in NSCLC cell viability.

6.9 Example 9

Clinical studies are conducted to assess the ability of a cytidine analog, such as 5-azacytidine, to treat patients having NSCLC (including, e.g., the ability to stop or reverse the growth of particular NSCLC cell types in patients having NSCLC). In certain clinical studies, patients are tested for particular NSCLC cell types, e.g., A549, H1975, H23, H460, and H1299, prior to administration of 5-azacytidine. In such studies, patients with cell types known to benefit preferentially from 5-azacytidine administration are enrolled. In other clinical studies, patients having NSCLC are enrolled without analysis of particular NSCLC cell type. In such studies, patients having any type of NSCLC cells are candidates for treatment with 5-azacytidine.

In certain clinical studies, patients from any of the three main NSCLC groups may be enrolled, i.e., (1) patients with tumors that are surgically resectable; (2) patients with either locally or regionally advanced lung cancer; or (3) patients with distant metastases at the time of diagnosis. In such studies, patients may be currently undergoing one or more additional treatment for NSCLC, including, e.g., surgery, chemotherapy, immunotherapy, targeted therapy, and radiation therapy.

The amount of azacytidine administered in the clinical studies depends, e.g., on the individual characteristics of the patient, including, inter alia, the stage and progression of the patient's NSCLC, the patient's age and weight, the patient's prior treatment regimens, and other variables as known in the art. A potential starting dose for the first treatment cycle may be about 75 mg/m$^2$ daily for 7 days, to be administered by subcutaneous (SC) injection or intravenous (IV) infusion. Cycles may be repeated every few weeks. After a certain number of cycles, the dosage may increase to 100 mg/m$^2$ if no beneficial effect is seen and no toxicity other than nausea and vomiting has occurred. Patients may be treated for a minimum of 4 to 6 cycles. Complete or partial response may require additional treatment cycles. Treatment may be continued as long as the patient continues to benefit.

All publications and patents cited and/or discussed in the above specification are herein incorporated by reference in their entirety. The present disclosure has been described in connection with certain embodiments and examples; however, unless otherwise indicated, the claimed invention should not be unduly limited to such specific embodiments and examples.

What is claimed is:

1. A method for treating a subject having non-small cell lung cancer by administering to the subject 5-azacytidine or a pharmaceutically acceptable salt, solvate, or hydrate thereof.

2. The method of claim 1, wherein the 5-azacytidine or a pharmaceutically acceptable salt, solvate, or hydrate thereof is administered orally.

3. The method of claim 1, wherein the 5-azacytidine or a pharmaceutically acceptable salt, solvate, or hydrate thereof is administered parenterally.

4. The method of claim 1, wherein the 5-azacytidine or a pharmaceutically acceptable salt, solvate, or hydrate thereof is administered topically.

5. The method of claim 1, wherein the 5-azacytidine is present in an amount sufficient to provide a daily dosage of up to about 500 mg/m$^2$.

6. A method for treating a subject having non-small cell lung cancer by administering to the subject a pharmaceutical composition comprising 5-azacytidine or a pharmaceutically acceptable salt, solvate, or hydrate thereof.

7. The method of claim 6, wherein the pharmaceutical composition is administered orally.

8. The method of claim 6, wherein the pharmaceutical composition is administered parenterally.

9. The method of claim 6, wherein the pharmaceutical composition is administered topically.

10. The method of claim 6, wherein the pharmaceutical composition comprises 5-azacytidine in an amount sufficient to provide a daily dosage of up to about 500 mg/m$^2$.

11. The method of claim 1, wherein the method further comprises co-administering to the subject an additional cancer therapeutic agent.

12. The method of claim 1, wherein the subject is a human.

13. The method of claim 1, wherein the non-small cell lung cancer comprises a non-small cell lung cancer cell type.

14. The method of claim 13, wherein the cell type is A549.

15. The method of claim 13, wherein the cell type is H1975.

16. The method of claim 13, wherein the cell type is H23.

17. The method of claim 13, wherein the cell type is H460.

18. The method of claim 13, wherein the cell type is H1299.

19. The method of claim 1, wherein the method comprises identifying in the subject the presence of a non-small lung cancer cell type, and administering 5-azacytidine to the subject.

20. The method of claim 19, wherein the cell type is A549.

21. The method of claim 19, wherein the cell type is H1975.

22. The method of claim 19, wherein the cell type is H23.

23. The method of claim 19, wherein the cell type is H460.

24. The method of claim 19, wherein the cell type is H1299.

25. The method of claim 1, wherein the non-small cell lung cancer comprises a cell type that is sensitive to 5-azacytidine.

26. The method of claim 1, wherein the non-small cell lung cancer comprises a cell type in which 5-azacytidine induces histone H2AX phosphorylation.

27. The method of claim 1, wherein the non-small cell lung cancer comprises a cell type in which 5-azacytidine induces DNA damage.

28. The method of claim 1, wherein the non-small cell lung cancer comprises a cell type in which 5-azacytidine induces PARP cleavage.

29. The method of claim 1, wherein the non-small cell lung cancer comprises a cell type in which 5-azacytidine induces cell death.

30. The method of claim 1, wherein the non-small cell lung cancer comprises a cell type in which 5-azacytidine induces cells having positive AnnexinV staining.

31. The method of claim 1, wherein the non-small cell lung cancer comprises a cell type in which 5-azacytidine induces an accumulation of cells in the sub-G1 phase.

32. The method of claim 1, wherein the non-small cell lung cancer comprises a cell type in which 5-azacytidine induces differential gene expression.

* * * * *

UNITED STATES PATENT AND TRADEMARK OFFICE
CERTIFICATE OF CORRECTION

PATENT NO. : 8,492,361 B2
APPLICATION NO. : 13/148636
DATED : July 23, 2013
INVENTOR(S) : Nguyen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 55 days.

Signed and Sealed this
Twenty-second Day of October, 2013

Teresa Stanek Rea
*Deputy Director of the United States Patent and Trademark Office*